United States Patent
Lai et al.

(10) Patent No.: US 10,100,102 B2
(45) Date of Patent: Oct. 16, 2018

(54) COMPOSITIONS AND METHODS FOR INHIBITING PATHOGEN INFECTION

(71) Applicants: The University of North Carolina at Chapel Hill, Chapel Hill, NC (US); The Johns Hopkins University, Baltimore, MD (US)

(72) Inventors: Samuel Lai, Carrboro, NC (US); Ying-Ying Wang, Baltimore, MD (US); Arthi Kannan, Morrisville, NC (US); Kennetta Nunn, Durham, NC (US); Durai Babu Subramani, Chapel Hill, NC (US); Richard Cone, Baltimore, MD (US)

(73) Assignees: The University of North Carolina at Chapel Hill, Chapel Hill, NC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/438,511

(22) PCT Filed: Oct. 29, 2013

(86) PCT No.: PCT/US2013/067328
§ 371 (c)(1),
(2) Date: Apr. 24, 2015

(87) PCT Pub. No.: WO2014/070786
PCT Pub. Date: May 8, 2014

(65) Prior Publication Data
US 2015/0284451 A1    Oct. 8, 2015

Related U.S. Application Data

(60) Provisional application No. 61/719,689, filed on Oct. 29, 2012.

(51) Int. Cl.
| | | |
|---|---|---|
| *C07K 16/08* | (2006.01) | |
| *A61K 39/395* | (2006.01) | |
| *C07K 16/12* | (2006.01) | |
| *C07K 16/18* | (2006.01) | |
| *A61K 39/00* | (2006.01) | |

(52) U.S. Cl.
CPC ........ *C07K 16/1235* (2013.01); *C07K 16/087* (2013.01); *C07K 16/18* (2013.01); *A61K 2039/505* (2013.01); *C07K 2317/41* (2013.01); *C07K 2317/71* (2013.01); *C07K 2317/72* (2013.01)

(58) Field of Classification Search
None
See application file for complete search history.

(56) References Cited

U.S. PATENT DOCUMENTS

| | | | | |
|---|---|---|---|---|
| 6,045,786 A | * | 4/2000 | Cone | C07K 16/00 424/134.1 |
| 6,355,235 B1 | * | 3/2002 | Cone | C07K 16/00 424/134.1 |
| 2006/0083741 A1 | * | 4/2006 | Hoffman | A61K 39/39541 424/145.1 |
| 2006/0131350 A1 | * | 6/2006 | Schechter | A61M 15/009 222/645 |
| 2006/0198848 A1 | | 9/2006 | Betz et al. | |
| 2008/0060092 A1 | * | 3/2008 | Dickey | C07K 14/47 800/276 |
| 2010/0008905 A1 | * | 1/2010 | Burioni | A61K 39/21 424/131.1 |
| 2011/0318376 A1 | * | 12/2011 | Murata | A61K 39/155 424/186.1 |

FOREIGN PATENT DOCUMENTS

| | | | |
|---|---|---|---|
| WO | WO 9201473 A1 * | 2/1992 | ........ C07K 16/1027 |
| WO | WO 2006/012539 A1 | 2/2006 | |
| WO | WO 2006/135309 A2 | 12/2006 | |
| WO | WO 2012/078877 A2 | 6/2012 | |

OTHER PUBLICATIONS

Olmsted SS, Padgett JL, Yudin AI, Whaley KJ, Moench TR, Cone RA. Diffusion of macromolecules and virus-like particles in human cervical mucus. Biophys J. Oct. 2001;81(4):1930-7.*

Lai SK, Wang YY, Hida K, Cone R, Hanes J. Nanoparticles reveal that human cervicovaginal mucus is riddled with pores larger than viruses. Proc Natl Acad Sci U S A. Jan. 12, 2010;107(2):598-603. doi: 10.1073/pnas.0911748107. Epub Dec. 16, 2009. Erratum in: Proc Natl Acad Sci U S A. Aug. 23, 2011;108(34):14371.*

Parr EL, Bozzola JJ, Parr MB. Immunity to vaginal infection by herpes simplex virus type 2 in adult mice: characterization of the immunoglobulins in vaginal mucus. J Reprod Immunol. Apr. 1998;38(1):15-30.*

Hobbs SM, Jackson LE, Hoadley J. Interaction of aglycosyl immunoglobulins with the IgG Fc transport receptor from neonatal rat gut: comparison of deglycosylation by tunicamycin treatment and genetic engineering. Mol Immunol. Jul.-Aug. 1992;29(7-8):949-56.*

Ghirlando R, Lund J, Goodall M, Jefferis R. Glycosylation of human IgG-Fc: influences on structure revealed by differential scanning micro-calorimetry. Immunol Lett. May 3, 1999;68(1):47-52.*

(Continued)

*Primary Examiner* — Stacy B Chen
(74) *Attorney, Agent, or Firm* — Myers Bigel, P.A.

(57) ABSTRACT

The presently-disclosed subject matter relates to antibodies, compositions, and methods for inhibiting and treating pathogen infection and providing contraception. In particular, the presently-disclosed subject matter relates to inhibiting and treating pathogen infection and providing contraception in a subject using compositions and antibodies capable of trapping pathogens or sperm in mucus, thereby inhibiting transport of pathogens or sperm across mucus secretions. The subject matter further relates to methods for monitoring the effectiveness of vaccines by detecting antibodies capable of trapping pathogens in mucus.

14 Claims, 9 Drawing Sheets

(56) References Cited

OTHER PUBLICATIONS

Carragher et al., The Journal of Immunology, 2008, 181:4186-4176.*
Nelson et al., Nature Reviews, Drug Discovery, Oct. 2010, 9:767-774.*
Labrijn A. F. and Parren W. H. I., 1999, Neutralizing epitopes of HIV-1, p. 13-34, in B. Korber, C. Brander, B. F. Haynes, J. P. Moore, R. Koup, B. Walker, and D. I. Watkins (ed.), HIV Molecular Immunology database, Los Alamos National Laboratory, Los Alamos, New Mexico, also available from https://www.hiv.lanl.gov/content/sequence/HIV/REVIEWS/art.*
Bomsel et al. "Immunization with HIV-1 gp41 Subunit Virosomes Induces Mucosal Antibodies Protecting Nonhuman Primates against Vaginal SHIV Challenges", *Immunity* 34:269-280 (2011).
Whaley et al. "Emerging antibody products and Nicotiana manufacturing", *Human Vaccines* 7(3):349-356 (2011).
Xu et al. "Passive immunization with human neutralizing monoclonal antibodies: correlates of protective immunity against HIV", *Vaccine* 20:1956-1960 (2002).
Notification of Transmittal of the International Search Report and the Written Opinion of the International Searching Authority, or the Declaration corresponding to International Application No. PCT/US2013/067328 dated Mar. 13, 2014.
Dudley et al. "Immune Protection against HSV-2 in B-Cell-Deficient Mice", *Virology* 270:454-463 (2000).
Fahrbach et al. "Differential Binding of IgG and IgA to Mucus of the Female Reproductive Tract", *PLOS One* 8(10)e76176 (2013) 11 pages.
Hansen et al. "Antibodies in the small intestine: mucosal synthesis and deposition of anti-glycosyl IgA, IgM, and IgG in the enterocyte brush border", *Am. J. Physiol. Gastrointest. Liver Physiol.* 291:G82-G90 (2006).
Kannan et al. "Mucosal immunity mediated by antibody-mucin cross-linking", *Glycobiology, Oxford University Press* 22(11):1537-1538 (2012).

Mascola et al. "Protection of macaques against vaginal transmission of a pathogenic HIV-1/SIV chimeric virus by passive infusion of neutralizing antibodies", *Nature Medicine* 6(2):207-210 (2000).
Saltzman et al. "Long-Term Vaginal Antibody Delivery: Delivery Systems and Biodistribution", *Biotechnol Bioeng* 67:253-264 (2000).
European Search Report corresponding to European Application No. 13851374.2 dated May 4, 2016.
Chen et al. "Transient Antibody-Mucin Interactions Produce a Dynamic Molecular Shield against Viral Invasion", *Biophysical Journal* 108:2028-2036 (2014).
Cosio et al. "Binding of human fibronectin to antigen-antibody complexes", *The Journal of Laboratory and Clinical Medicine* 107(5):453-458 (1986) Abstract Only (2 pages).
Notification of Transmittal of the International Search Report and the Written Opinion of the International Searching Authority, or the Declaration corresponding to International Application No. PCT/US2016/061574 dated Feb. 27, 2017.
Desoubeaux et al. "Therapeutic monoclonal antibodies for respiratory diseases: Current challenges and perspectives, Mar. 31-Apr. 1, 2016, Tours, France", *MABS* 8(6):999-1009 (2016).
Ercan et al. "Multiple juvenile idiopathic arthritis subtypes demonstrate pro-inflammatory IgG glycosylation"; Arthritis Rheum. 64(9):3025-3033 (2012).
Fellner et al. "Inhaled protein/peptide-based therapies for respiratory disease", Molecular and Cellular Pediatrics 3:16 pp. 1-5 (2016).
Karsten et al. "Anti-inflammatory activity of IgG1 mediated by Fc galactosylation and association of FcγRIIB and dectin-1", Nature Medicine 18(9):1401-1409 (2012).
Maverakis et al. "Glycans in the Immune system and The Altered Glycan Theory of Autoimmunity: A critical review" Journal of Autoimmunity 57:1-13 (2015).
Prince et al. "Treatment of Respiratory Syncytial Virus Bronchiolitis and Pneumonia in a Cotton Rat Model with Systemically Administered Monoclonal Antibody (Palivizumab) and Glucocorticosteroid", The Journal of Infectious Diseases 182:1326-30 (2000).
Rimensberger et al. "Aerosolized immunoglobulin treatment of respiratory syncytial virus infection in infants", The Pediatric Infectious Disease Journal 15(3)209-216 (1996) Abstract Only.

* cited by examiner

FIG. 2

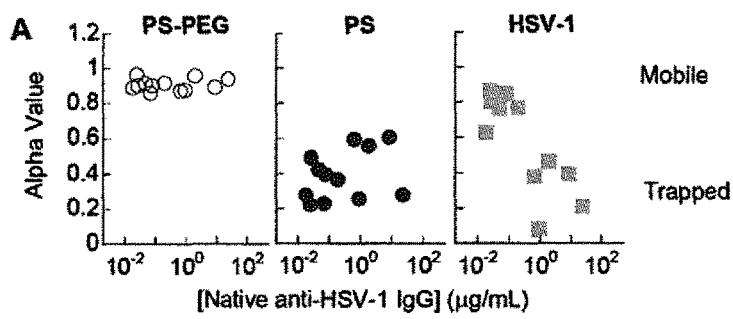

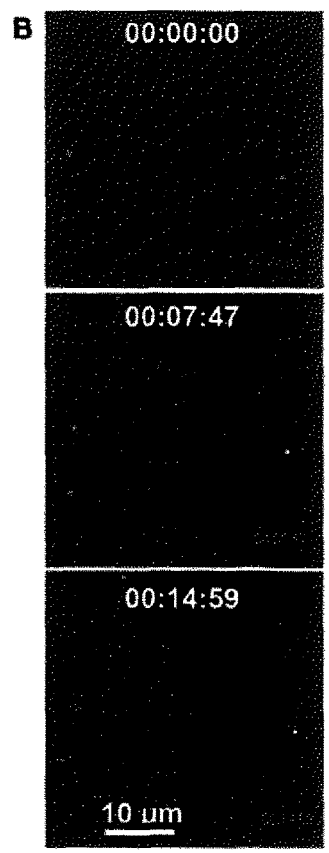

Average α values for PS-PEG, PS and HSV-1 in native or Ab-treated CVM

| Particle | Treatment | n | α |
|---|---|---|---|
| PS-PEG | Native (low endogenous anti-HSV-1 IgG) | 7 | 0.91 ± 0.012 |
| PS-PEG | Native (high endogenous anti-HSV-1 IgG) | 5 | 0.91 ± 0.016 |
| PS | Native (low endogenous anti-HSV-1 IgG) | 7 | 0.34 ± 0.039 |
| PS | Native (high endogenous anti-HSV-1 IgG) | 5 | 0.46 ± 0.078 |
| HSV-1 | Native (low endogenous anti-HSV-1 IgG) | 7 | 0.79 ± 0.031 |
| HSV-1 | Native (high endogenous anti-HSV-1 IgG) | 5 | 0.31 ± 0.071 * |
| HSV-1 | 33 ng/mL anti-HSV-1 IgG | 7 | 0.67 ± 0.029 * |
| HSV-1 | 100 ng/mL anti-HSV-1 IgG | 7 | 0.48 ± 0.074 * |
| HSV-1 | 333 ng/mL anti-HSV-1 IgG | 7 | 0.32 ± 0.046 * |
| HSV-1 | 1000 ng/mL anti-HSV-1 IgG | 7 | 0.31 ± 0.045 * |
| HSV-1 | Native (low endogenous anti-HSV-1 IgG) | 5 | 0.76 ± 0.059 |
| HSV-1 | Anti-HSV-1 IgG | 5 | 0.35 ± 0.054 * |
| HSV-1 | Deglycosylated anti-HSV-1 IgG | 4 | 0.62 ± 0.10 |
| HSV-1 | Anti-HSV-1 F(ab')$_2$ | 4 | 0.59 ± 0.063 |

†Values are expressed as mean ± SEM
* indicates $p < 0.01$ compared to "Native (low endogenous anti-HSV-1 IgG)" group; based on Student's t-test (paired for comparisons of Ab-treated vs. native CVM for the same CVM samples)

COMPOSITIONS AND METHODS FOR INHIBITING PATHOGEN INFECTION

STATEMENT OF PRIORITY

This application is a 35 U.S.C. § 371 national phase application of PCT Application No. PCT/US2013/067328 filed Oct. 29, 2013, which claims the benefit of U.S. Provisional Application Ser. No. 61/719,689, filed Oct. 29, 2012, the entire contents of each of which is incorporated by reference herein.

GOVERNMENT INTEREST

This invention was made with government support under Grant Numbers R21AI093242 and U19AI096398 awarded by the National Institutes of Health. The government has certain rights in the invention.

FIELD OF THE INVENTION

The presently-disclosed subject matter relates to antibodies, compositions, and methods for inhibiting and treating pathogen infection and providing contraception. In particular, the presently-disclosed subject matter relates to inhibiting and treating pathogen infection and providing contraception in a subject using compositions and antibodies that trap pathogens in mucus, thereby inhibiting transport of pathogens or sperm across or through mucus secretions. The subject matter further relates to methods for monitoring the effectiveness of vaccines by detecting antibodies capable of trapping pathogens in mucus.

BACKGROUND OF THE INVENTION

Large quantities of IgG are transported into female genital tract mucus secretions by the MHC class I-related neonatal Fc receptor (Li et al., *Proc. Natl. Acad. Sci. U.S.A.* 108:4388 (2011), resulting in at least ten-fold more IgG than IgA (Usala et al., *J. Reprod. Med.* 34:292 (1989)). However, despite this predominance of IgG, the precise mechanism(s) by which secreted IgG can prevent vaginal infections are not well understood. Previous animal studies have shown that antibodies (Ab) can provide robust protection against vaginal challenge with pathogens, including human immunodeficiency virus (HIV) and herpes simplex virus-2 (HSV-2), when applied intravaginally (Burton et al., *Proc. Natl. Acad. Sci. U.S.A.* 108:11181 (2011); Sherwood et al., *Nature Biotechnol.* 14:468 (1996); Veazey et al., *Nature Med.* 9:343 (2003); Whaley et al., *J. Infect. Dis,* 169:647 (1994)) or even intravenously (Hessell et al., *PLoS Pathogens* 5:e1000433 (2009); Mascola et al., *Nature Med.* 6:207 (2000)). Many investigators have focused on neutralizing Ab, which, at sufficiently high doses, provided sterilizing immunity against simian-human immunodeficiency virus (SHIV) challenge in rhesus macaques (Burton et al., *Proc. Natl. Acad. Sci. U.S.A.* 108:11181 (2011)). In the same studies, non-neutralizing or poorly neutralizing Ab provided at best only partial protection, with some infected animals exhibiting reduced viral load. Studies by Hessell et al. and Mascola et al. showed complete protection in some animals even by weakly neutralizing antibodies, as well as reduced viremia in others (Hessell et al., *PLoS Pathogens* 5:e1000433 (2009); Mascola et al., *Nature Med.* 6:207 (2000)).

Few studies have explored the potential protective role of IgG within the mucus secretions overlaying the epithelial tissue, which sexually transmitted viruses invariably encounter and must penetrate in order to reach target cells. Well-known Ab effector functions in blood and lymph (e.g., complement activation, opsonization, and ADCC) are absent or limited in healthy female genital secretions, which typically have little complement activity and few if any active leukocytes (Cone, In *Handbook of Mucosal Immunology*. P. L. Ogra et al., editors. Academic Press, San Diego, Calif. 43-64 (1999); Hill et al., *Am. J. Obstet. Gynecol.* 166:720 (1992); Schumacher, *Hum. Reprod.* 3:289 (1988)). These classical mechanisms of systemic immune protection do not adequately account for the moderate but significant protection observed in the landmark Thai RV144 HIV vaccine trial (Kresge, *IAVI Report Vol* 13, Number 5 (2009); Rerks-Ngarm et al., *N. Engl. J. Med.* 361:2209 (2009)). The vaccination regimen modestly reduced the risk of HIV acquisition despite inducing primarily non-neutralizing Ab and otherwise offering little to no protection against systemic progression of infections once acquired, suggesting that protection likely occurred prior to initiation of infection. A better understanding of potential additional mechanisms of vaginal mucosal immunity will also likely be critical for developing effective vaccines against other sexually transmitted infections, including HSV, which has been shown to evade complement and other classical antibody-mediated protective mechanisms (Brockman et al., *Vaccine* 26 *Suppl* 8:194 (2008); Hook et al., *J. Virol.* 80:4038 (2006); Lubinski et al., *J. Exp. Med.* 190:1637 (1999)). To date, herpes vaccine candidates have achieved only transient and partial protection despite inducing high neutralizing serum antibody titers and cellular immunity (Chentoufi et al., *Clin. Dev. Immunol.* 2012:187585 (2012)). A Phase III clinical trial, using a subunit vaccine based on HSV-2 glycoprotein D, demonstrated some protection against HSV-1 infection but no efficacy against HSV-2 infection and no overall efficacy against genital disease (Belshe et al., *New Eng. J. Med.* 366:34 (2012)).

There is a need in the art for new compositions, and methods of using such compositions, to prevent and treat infectious diseases and provide contraception.

SUMMARY OF THE INVENTION

Viruses must penetrate cervicovaginal mucus (CVM) to reach and infect their target cells in the vaginal epithelium; indeed, HIV and human papillomavirus (HPV) are both capable of rapidly diffusing through human genital mucus secretions (Lai et al., *J. Virol.* 83:11196 (2009); Olmsted et al., *Biophys. J.* 81:1930 (2001)). It was previously found that the diffusion of IgG (11 nm) was slowed slightly in human cervical mucus compared to saline buffer, while much larger virus-like particles, including the capsids of norovirus (38 nm) and HPV (55 nm), were not slowed by this mucus (Olmsted et al., *Biophys. J.* 81:1930 (2001)). It was hypothesized that the slight retardation of the much smaller IgG molecules may be due to very transient (<1 s), low-affinity bonds with the mucin mesh (Olmsted et al., *Biophys. J.* 81:1930 (2001)). In other words, by making only transient low-affinity bonds with mucins, IgG is able to diffuse rapidly through mucus, and in theory is therefore free to quickly accumulate on a pathogen surface.

These observations prompted the discovery that the array of Ab bound to the pathogen surface can effectively trap the pathogen in mucus gel by ensuring at least some low-affinity bonds to the mucin mesh are present at any given time (FIG. 13). Virions trapped in CVM cannot reach their target cells, and will instead be shed with post-coital discharge and/or inactivated by spontaneous thermal degradation as well as additional protective factors in mucus, such as defensins (Cole, *Curr. Top. Microbiol. Immunol.* 306:199 (2006); Doss et al., *J. Leukoc. Biol.* 87:79 (2010). This discovery provides novel methods for preventing and treating infection, monitoring the effectiveness of vaccines, and providing contraception.

Thus, one aspect of the invention relates to an isolated antibody comprising an oligosaccharide at a glycosylation site, the oligosaccharide comprising a glycosylation pattern that enhances trapping potency of the antibody in mucus, wherein the antibody specifically binds an epitope of a target pathogen or sperm.

A further aspect of the invention relates to compositions, e.g., pharmaceutical compositions, and kits comprising the antibodies of the invention.

An additional aspect of the invention relates to a method of inhibiting an infection by a pathogen or a disease or disorder caused by an infection by a pathogen in a subject in need thereof, comprising administering to a mucosa of the subject the antibody of the invention in an amount effective to inhibit an infection.

Another aspect of the invention relates to a method of treating an infection by a pathogen or a disease or disorder caused by an infection by a pathogen in a subject in need thereof, comprising administering to a mucosa of the subject the antibody of the invention in an amount effective to treat the infection.

A further aspect of the invention relates to a method of providing contraception in a female subject, comprising administering to a mucosa of a reproductive tract of the subject the antibody of the invention in an amount effective to provide contraception, wherein the antibody specifically binds an epitope of sperm.

An additional aspect of the invention relates to a method of monitoring the effectiveness of a vaccination in a subject that has been vaccinated against a target pathogen, comprising determining in a mucus sample from said subject the amount of an antibody comprising an oligosaccharide at a glycosylation site, the oligosaccharide having a glycosylation pattern that enhances trapping potency of the antibody in mucus, wherein the antibody specifically binds an epitope of said target pathogen.

These and other aspects of the invention are set forth in more detail in the description of the invention below.

BRIEF DESCRIPTION OF THE DRAWINGS

FIGS. 2A-2B show transport characteristics for control beads and HSV-1 in CVM. (A) Alpha (a) values for control beads (PS-PEG and PS) and HSV-1 in individual CVM samples from unique donors (n=12, each experiment performed independently) as a function of endogenous anti-HSV-1 IgG. α is the slope of the log-log mean square displacement (<MSD>) vs. time scale plot (α=1 for pure unobstructed Brownian diffusion, e.g., particles in water, and α becomes smaller as obstruction to particle diffusion increases). Alpha values from all tracking analyses are listed in the table. (B) HSV-1 virions trapped in CVM at short time scales remain similarly immobilized even at long time scales. HSV-1 in CVM sample with elevated endogenous anti-HSV-1 IgG remain confined to the same locations over more than 15 min. Time stamps (bottom right corner, magnified at top center; hh:mm:ss) indicate elapsed time in three images from a representative movie.

FIGS. 10A-10B show mobility of individual *Salmonella typhimurium* bacteria in control or anti-LPS monoclonal IgG-treated mouse gastrointestinal mucus. (A) Microscopy setup that enables measurement of bacterial mobility in real time directly in mucus overlaying intestinal epithelial tissue excised from mice. The epithelium was NOT subjected to washing and hence the physiological mucus layer is intact. (B) The fraction of motile *Salmonella typhimurium* and their velocities in mucus overlaying different parts of the GI tract in native vs. anti-LPS IgG1 treatment. Similar findings were observed with anti-flagella Ab as well as with IgG2a.

DETAILED DESCRIPTION OF THE INVENTION

Figure 1:
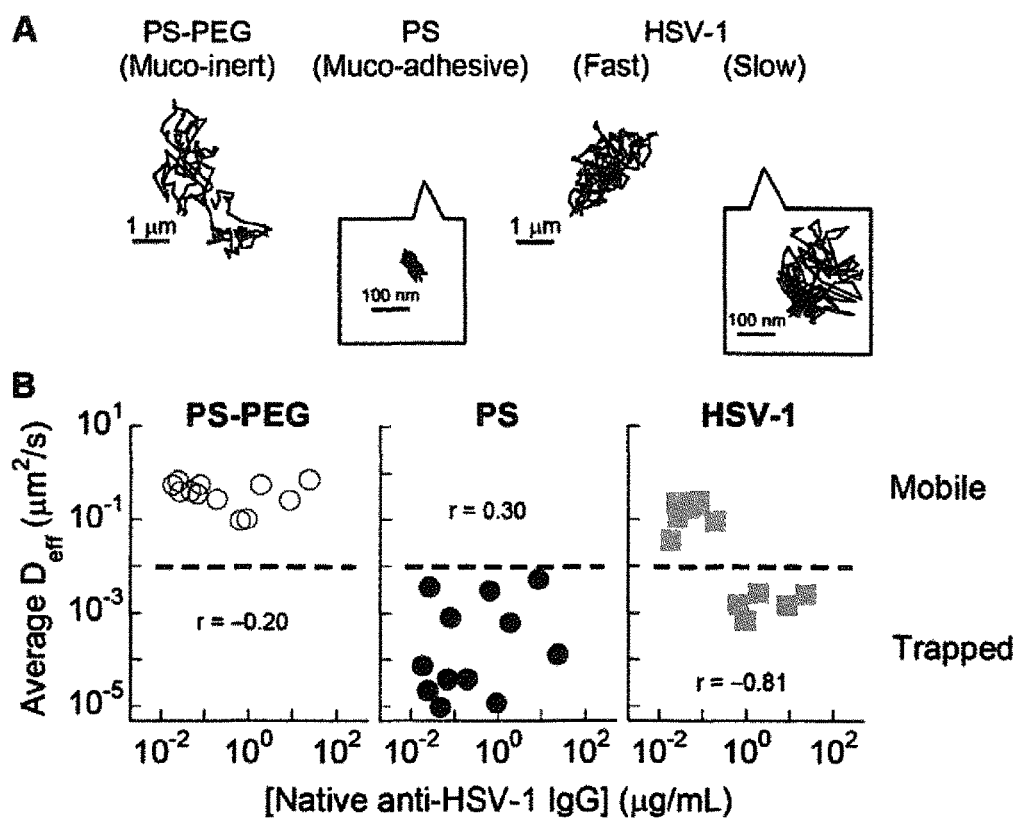
FIGS. 1A-1B show HSV-1 is immobilized in CVM samples with elevated endogenous anti-HSV-1 IgG but readily mobile in samples with low endogenous anti-HSV-1 IgG. Fluorescent HSV-1 or control particles were added to CVM, and their motions were analyzed by multiple particle tracking methods. (A) Representative 20 s traces of HSV-1 (d~180 nm) and control particles (d~200 nm) with effective diffusivity ($D_{eff}$) at a time scale r of 1 s within one SEM of the mean. Control particles include muco-inert (PEG-coated; PS-PEG) and muco-adhesive (uncoated; PS) polystyrene beads, which are freely diffusive and trapped in human CVM, respectively. (B) Geometric average $D_{eff}$ ($\tau=1$ s) for PS-PEG, PS and HSV-1 in individual CVM samples from unique donors (n=12, each experiment performed independently) as a function of endogenous anti-HSV-1 IgG. Dashed lines represent the $D_{eff}$ cutoff below which particles are permanently trapped (moving less than their diameter within 1 s). Pearson's correlation coefficients (r) are indicated.

The present invention is based, in part, on the discovery and characterization of weak binding interactions between antibodies and mucins and the ability of such antibodies to stop the penetration of pathogens through mucus layers. The antibody-mucin interaction can be used advantageously in methods for preventing and treating infection, providing contraception, and monitoring the effectiveness of vaccines.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

I. Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03.

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" antibody means an antibody separated or substantially free from at least some of the other components of the naturally occurring organism or virus, for example, the cell structural components or other polypeptides or nucleic acids commonly found associated with the antibody. The term also encompasses antibodies that have been prepared synthetically.

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

As used herein, the term "trapping potency" refers to the ability of an antibody that specially binds to a target pathogen or sperm to inhibit movement of the pathogen or sperm through mucus. Trapping potency can be measured by methods known in the art and as disclosed herein. Trapping potency can be quantitated, e.g., as the amount of antibody (e.g., concentration of antibody in mucus) needed to reduce the mobility of at least 50% of the pathogen or sperm within the mucus gel to at least one-tenth of its mobility in solution (e.g., saline). Mobility in mucus can be measured using techniques well known in the art and described herein. Alternatively, trapping potency can be quantitated as the reduction in percentage of pathogens or sperm that penetrate mucus.

The term "enhances trapping potency" refers to an antibody comprising an oligosaccharide that provides an increased trapping potency relative to the trapping potency of antibodies as found in nature and/or antibodies prior to any modification and/or selection.

As used herein, the term "bind specifically" or "specifically binds" in reference to an antibody of the presently-disclosed subject matter means that the antibody of the invention will bind with an epitope (including one or more epitopes) of a target pathogen or sperm, but does not substantially bind to other unrelated epitopes or molecules. In certain embodiments, the term refers to an antibody that exhibits at least about 60% binding, e.g., at least about 70%, 80%, 90%, or 95% binding, to the target epitope relative to binding to other unrelated epitopes or molecules.

II. Antibodies and Compositions

The presently-disclosed subject matter includes antibodies, compositions, and methods for inhibiting and/or treating pathogen infection, eliminating pathogen from a mucosal surface, providing contraception, and/or monitoring the effectiveness of vaccines. In particular, the presently-disclosed subject matter relates to antibodies and compositions capable of trapping pathogens and sperm in mucus, thereby inhibiting transport of pathogens or sperm across or through mucus secretions.

The prevailing view of how antibodies protect a subject at mucosal surfaces assumes that neutralization of the pathogen is the primary mechanism of protection. Surprisingly and unexpectedly, in light of this widespread view, the present inventors disclose herein that neutralization is not necessary to protect against infection at mucosal surfaces in a subject. Indeed, it is demonstrated herein that sub-neutralization doses of antibodies to neutralizing epitopes of pathogens can be quite effective at inhibiting infection. Furthermore, it is demonstrated herein that use of antibodies to non-neutralizing epitopes of pathogens can also be quite effective at inhibiting infection.

Antibodies are naturally found in mucus. The current thoughts on antibody-mediated mucosal protection are that secretory IgA (sIgA) antibodies are important for protection because very large amounts of this isotype are found in the gastrointestinal tract. It is further thought that IgG does not play a role in mucosal protection. However, IgG is the dominant isotype in genital secretions and there is approximately a 50:50 ratio of IgG:IgA in respiratory mucus secretions. In contrast to the prevailing thought in the scientific community, it is shown herein that certain antibodies, e.g., IgG, found in CVM can diffuse rapidly through the CVM, slowed only slightly by weak, transient adhesive interactions with mucins within the mucus. This rapid diffusion allows antibodies to accumulate rapidly on pathogen or sperm surfaces. When a plurality of antibodies have accumulated on the surface of a pathogen, the adhesive interactions between the plurality of antibodies and the mucus become sufficient to trap the bound pathogen or sperm in the mucus, thereby preventing infection/providing contraception. Pathogens or sperm trapped in CVM cannot reach their target cells in the mucosal surface, and will instead be shed with post-coital discharge and/or inactivated by spontaneous thermal degradation as well as additional protective factors in mucus, such as defensins (Cole, Curr. Top. *Microbiol. Immunol.* 306:199 (2006); Doss et al., *J. Leukoc. Biol.* 87:79 (2010). As disclosed herein, this pathogen trapping activity provides for protection without neutralization, and can effectively inhibit infection at sub-neutralization doses and/or using antibodies to non-neutralizing epitopes of a pathogen.

The present invention additionally provides the discovery that the low-affinity interactions that an antibody forms with mucins are not only Fc-dependent, but also influenced by antibody glycosylation.

Accordingly, the presently-disclosed subject matter includes an isolated antibody comprising an oligosaccharide at a glycosylation site, the oligosaccharide comprising, consisting essentially of, or consisting of a pattern correlating with (providing) enhanced trapping potency of the antibody in mucus, and wherein the antibody specifically binds an epitope of a target pathogen or sperm. The unique glycosylation pattern/unique oligosaccharide component of the antibody is designed to maximize trapping potency of the antibody once a plurality of antibodies are bound to the target pathogen or sperm, without unduly hindering the ability of the unbound antibody to diffuse readily through mucus to rapidly bind a target pathogen or sperm. In certain embodiments, the antibody is one that exhibits a mobility in mucus that is reduced no more than about 50%, e.g., no more than about 40%, 30, 20%, 10%, or 5%, relative to its mobility in solution (e.g., saline or water) and effectively traps a target pathogen or sperm in mucus based on a plurality of bound antibodies (e.g., at least 50% of pathogens or sperm slowed by at least 90%). In some embodiments, the antibody reduces the mobility of pathogens or sperm at least 50%, e.g., at least 60%, 70%, 80%, or 90% or more of the pathogen or sperm by at least 90%, e.g., at least 95%, 96%, 97%, 98%, or 99% or more. In other embodiments, the antibody reduces the percentage of pathogens or sperm that can penetrate mucus by at least 10%, e.g., at least 20%, 30%, 40%, 50%, 60%, 70%, 80%, 90%, or more. Based on the disclosure herein, one of skill in the art can readily identify/design oligosaccharide patterns that provide the desired trapping potency. In other embodiments, the antibody has a sufficient binding rate to an epitope of the target pathogen or sperm to accumulate on the surface of the target pathogen or sperm at sufficient levels to trap the target pathogen or sperm in mucus within one hour (e.g., within 30 minutes or 15 minutes) at an antibody concentration in the mucus of less than 5 µg/ml (e.g., less than 1 µg/ml or 0.1 µg/ml).

In some embodiments, the oligosaccharide component is bound to an N-linked glycosylation site in an Fc region of the antibody. The N-linked glycosylation site can be an asparagine residue on the Fc region of the antibody, for example, the Asn 297 asparagine residue. The amino acid numbering is with respect to the standard amino acid structure of a human IgG molecule.

Figure 12:
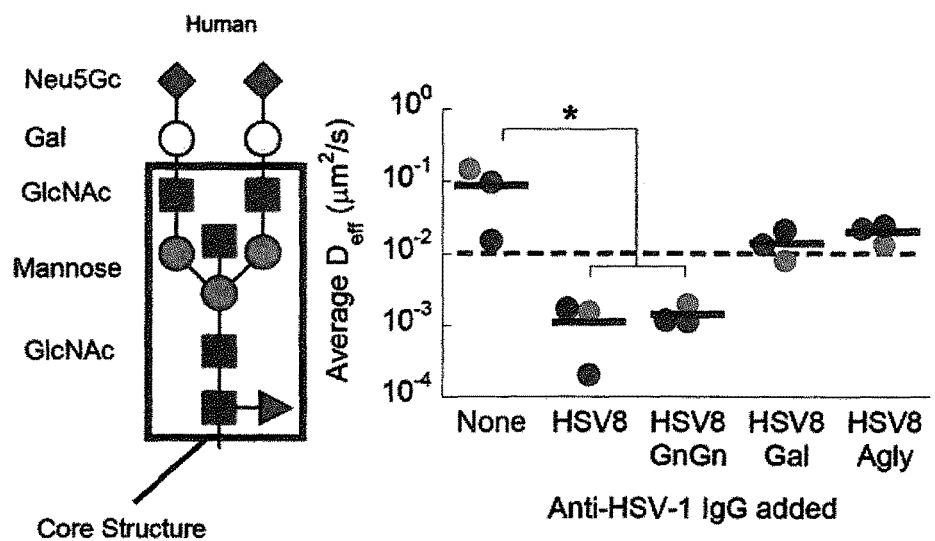
FIG. 12 shows the role of N-glycans in IgG-mucin interactions. In the oligosaccharide structure, the square is N-acetylglucosamine (GlcNAc), the triangle is fucose, the diamond is sialic acid (Neu5Gc), the light gray circle is galactose (Gal), and the dark gray circle is mannose.
Figure 13:
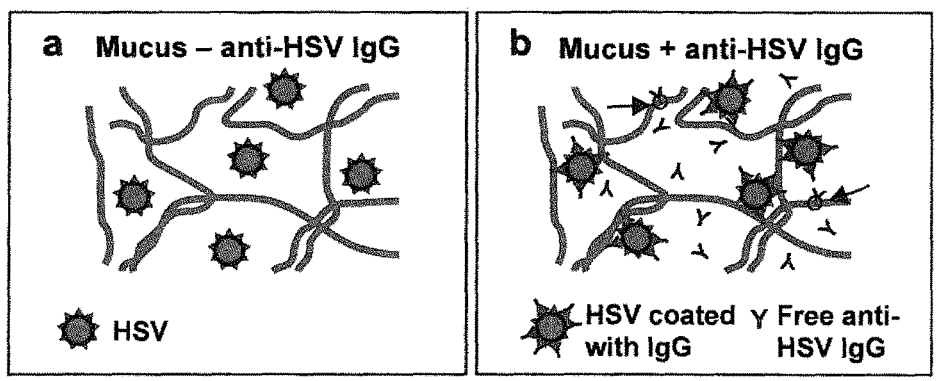
FIG. 13 shows the proposed mechanism of Ab-mediated trapping of viruses in mucus. Schematic showing (a) HSV readily penetrates native CVM with little to no endogenous anti-HSV IgG, and (B) anti-HSV IgG traps HSV in CVM by multiple transient, low affinity bonds with mucins. By forming only short-lived, low-affinity bonds with mucus, free Ab, such as IgG, are able to diffuse rapidly through mucus and binds to viruses. As IgG molecules accumulate on the virus surface, they form multiple low-affinity bonds between the virus and mucus gel. A sufficient number of these transient low-affinity bonds ensure viruses are effectively trapped in mucus at any given time, thereby reducing the flux of infectious virions that can reach target cells. Arrows indicate the small fraction of free (not virus-bound) IgG (~10-20%) that will interact with mucins at any moment in time.

The N-glycan structure on human IgG-Fc is typically dominated by a biantennary core structure that shares a common core sugar sequence (as shown in FIG. 12), Manα1-6(Manα1-3)Manβ1-4GlcNAcβ1-4GlcNAcβ1-Asn-X-Ser/Thr, with "antennae" initiated by N-acetylglucosaminyltransferases (GlcNAcTs) that help attach additional sugars to the core. In IgG found in human serum, the most common structures are those that contain both N-acetylglucosamine on each branch with one terminal galactose (39%), two terminal galactose (20%), or one terminal galactose and one terminal sialic acid (15%). Together, antibodies that comprise at least one terminal galactose represents about 74% of the IgG-Fc glycoforms. A pure GnGn form (with terminal N-acetylglucosamine on each branch without terminal galactose or sialic acid) represents about 26% of the IgG-Fc glycoforms.

In some embodiments, the oligosaccharide component, i.e., the glycan, attached to the antibody comprises, consists essentially of, or consists of the core structure depicted in FIG. 12. In some embodiments, the glycan attached to the antibody comprises, consists essentially of, or consists of the core structure depicted in FIG. 12 minus the fucose residue. In some embodiments, the glycan comprises, consists essentially of, or consists of the full structure depicted in FIG. 12. In other embodiments, the glycan does not contain any galactose residues. In certain embodiments, the glycan comprises the core structure as depicted in FIG. 12 and additional saccharide residues that do not include galactose. Without being limited by theory, it is believed that the presence of galactose compromises trapping potency. Antibodies with glycoforms that do not contain galactose represent just a small fraction of the entire repertoire of glycoforms found in nature. The use of a population of antibodies enriched with desirable glycoforms (whether naturally occurring or modified glycans) is advantageously used for trapping pathogens and sperm in mucus.

In some embodiments, the antibody of the invention is a mixture of antibodies having different oligosaccharide components. In some embodiments, the mixture of antibodies comprises at least about 30% antibodies having the core glycan structure depicted in FIG. 12 with or without the fucose residue, e.g., at least about 40%, 50%, 60%, 70%, 80%, 90% or more. In other embodiments, the mixture of antibodies comprises at least about 5% antibodies having the full glycan structure depicted in FIG. 12, e.g., at least about 10%, 20%, 30%, 40%, 50%, 60%, 70%, 80%, 90% or more. In some embodiments, the mixture of antibodies comprises at least about 30% antibodies having the core glycan structure depicted in FIG. 12, e.g., at least about 40%, 50%, 60%, 70%, 80%, 90% or more and at least about 5% antibodies having the full glycan structure depicted in FIG. 12, e.g., at least about 10%, 20%, 30%, 40%, 50%, 60%, 70%, 80%, 90% or more.

In some embodiments, the mixture of antibodies is the mixture generated in a human cell line, e.g., a 293 cell line, e.g., a 293T cell line.

The antibody is useful for binding target pathogens to trap the pathogen in mucus to inhibit infection by the pathogen. Target pathogens of the antibody can include any pathogen that can infect a subject through a mucus membrane. Pathogens can be in the categories of algae, bacteria, fungi, parasites (helminths, protozoa), viruses, and subviral agents. Target pathogens further include synthetic systems comprising an antigen having an epitope, for example particles or particulates (e.g., polystyrene beads) comprising attached proteins, e.g., as might be used for bioterrorism.

Pathogens include those that cause sexually-transmitted diseases (listed with the diseases caused by such pathogens), including, without limitation, *Neisseria gonorrhoeae* (gonorrhea); *Chlamydia trachomatis* (chlamydia, lymphogranuloma venereum); *Treponema pallidum* (syphilis); *Haemophilus ducreyi* (chancroid); *Klebsiella granulomatis* or *Calymmatobacterium granulomatis* (donovanosis), *Mycoplasma genitalium, Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus, hepatitis C virus (viral hepatitis); molluscum contagiosum virus (MCV); *Trichomona vaginalis* (trichomoniasis); and yeasts, such as *Candida albicans* (vulvovaginal candidiasis). The antibodies and compositions may also be active against other diseases that are transmitted by contact with bodily fluids that may also be transmissible by sexual contact and are capable of being prevented by administration of the compositions according to this invention. Accordingly, the phrase, "sexually transmitted diseases (STDs)," is to be interpreted herein as including any disease that is capable of being transmitted in the course of sexual contact, whether or not the genital organs are the site of the resulting pathology.

Pathogens also include those that cause respiratory diseases, including, without limitation, influenza (including influenza A, B, and C); severe acute respiratory syndrome (SARS); respiratory syncytial virus (RSV); parainfluenza; adenovirus; human rhinovirus; coronavirus; and norovirus.

Other pathogens include, without limitation, *Salmonella* and *Escherichia coli*.

Pathogens include those that affect non-human animals, such as livestock, e.g., swine (e.g., porcine epidemic diarrhea virus (PEDV), transmissible gastroenteritis virus (TGEV), rotavirus, classical swine fever virus (CSFV), porcine circovirus type 2 (PCV2), encephalomyocarditis virus (EMCV), porcine reproductive and respiratory syndrome virus (PRRSV), porcine parvovirus (PPV), pseudorabies virus (PRV), Japanese encephalitis virus (JEV), *Brucella, Leptospira, Salmonella*, and *Lawsonia intracellularis, Pasteurella multocida, Brachyspira hyodysenteriae, Mycoplasma hyopneumoniae*), ruminants (e.g., bovine virus diarrhoea virus (BVDV), border disease virus (BDV), bovine papular stomatitis virus (BPSV), pseudocowpox virus (PCPV), *Pasteurella haemolytica, Pasteurella multocida, Haemophilus somnus, Haemophilus agnii, Moraxella bovis, Mycoplasma mycoides, Theileria annulata, Mycobacterium avium paratuberculosis*), ungulates (e.g., *Brucella abortus, Mycobacterium bovis, Theileria parva*, Rift Valley fever virus, foot-and-mouth disease virus, lumpy skin disease virus), horses (e.g., *Rhodococcus equi, Salmonella choleraesuis, Pasteurella multocida*, equine herpesvirus-1, equine herpesvirus-4, equine influenza virus, *Streptococcus equi*), poultry (e.g., fowl pox virus, Newcastle disease virus, Marek's disease virus, avian influenza virus, infectious bursal disease virus (IBDV), avian infectious bronchitis virus (IBV)), and the like.

The terms virus and viral pathogen are used interchangeably herein, and further refer to various strains of virus, e.g., influenza is inclusive of new strains of influenza, which would be readily identifiable to one of ordinary skill in the art. The terms bacterium, bacteria, and bacterial pathogen are used interchangeably herein, and further refer to antibiotic-resistant or multidrug resistant strains of bacterial pathogens. As used herein when referring to a bacterial pathogen, the term "antibiotic-resistant strain" or "multidrug resistant strain" refers to a bacterial pathogen that is capable of withstanding an effect of an antibiotic or drug used in the art to treat the bacterial pathogen (i.e., a non-resistant strain of the bacterial pathogen).

In some embodiments, it is contemplated that an antibody according to the presently-disclosed subject matter is capable of broadly binding to viruses containing lipid envelopes, which are not necessarily specific to one virus.

As noted above, it was surprisingly discovered that sub-neutralization doses of an antibody can be used to effectively trap a target pathogen or sperm in mucus. As such, in some embodiments, wherein the antibody specifically binds a neutralizing epitope of the target pathogen, a sub-neutralization dose can be used. A sub-neutralization doses is a dose below that which would be needed to achieve effective neutralization. For example, in the case of polyclonal anti-HSV gG antibodies targeting HSV, as described hereinbelow, an effective neutralization dose is approximately 5

µg/ml. However, effective trapping using the antibody can be achieved at a dose below 5 µg/ml, and even below a dose of 1 µg/ml.

As will be recognized by one of skill in the art, doses appropriate for trapping bacterial pathogens can be higher in some embodiments than the doses appropriate for trapping viral pathogens. It will further be recognized that appropriate doses may differ between pathogens, between mucosal surfaces, and also between individuals. It will also be recognized that different subjects and different mucosal surfaces may have different optimal glycan patterns and optimal antibody-mucin affinities, contributing to different optimal doses.

It is further proposed herein that antibodies that selectively bind non-neutralizing epitopes of a target pathogen can be used to effectively trap the target pathogen in mucus. As such, in some embodiments, the antibody specifically binds a non-neutralizing epitope, e.g., one or more non-neutralizing epitopes.

The presently-disclosed subject matter further includes an antibody that selectively binds a conserved epitope of a target pathogen. A benefit of targeting a conserved epitope would be to preserve efficacy of the antibody as against new strains of the pathogen. Targeting such epitopes has been avoided at times in the past because they were viewed as being ineffective targets; however, in view of the disclosure herein that non-neutralizing epitopes can serve as effective targets and/or that sub-neutralization doses can be effective for inhibiting infection, previously dismissed conserved epitopes of target pathogens can be seen as effective targets.

Antibodies of the invention are useful for binding sperm to trap the sperm in mucus to inhibit fertilization of an egg by the sperm. Sperm specific antigens that can be used as antibody targets are well known in the art. See, e.g., U.S. Pat. Nos. 8,211,666, 8,137,918, 8,110,668, 8,012,932, 7,339,029, 7,230,073, and 7,125,550, each incorporated by reference in its entirety.

As noted above, it was determined that the low-affinity binding interactions that an antibody forms with mucins are influenced by antibody glycosylation, and are also Fc-dependent. As such, the presently-disclosed subject matter includes antibodies having a preserved and/or engineered Fc region. Such antibodies can be, for example, one or more of IgG, IgA, IgM, IgD, or IgE. In certain embodiments, the antibodies are IgG. In some embodiments, the antibodies are one or more subclasses of IgG, e.g., $IgG_1$, $IgG_2$, $IgG_3$, $IgG_4$, or any combination thereof.

In some embodiments, the antibody has a sufficient binding rate and/or binding affinity to an epitope of the target pathogen or sperm to accumulate on the surface of the pathogen or sperm at sufficient levels to trap the pathogen or sperm within one hour after administration of the antibody at an antibody concentration of less than about 5 µg/ml. The term "trap" in this instance refers to reduction of further movement through the mucus. In some embodiments, the target pathogen or sperm is trapped within about 30 minutes, e.g., about 25, 20, 15, or 10 minutes after administration of the antibody. In some embodiments, the antibody traps the target pathogen or sperm at an antibody concentration of less than about 4, 3, 2, or 1 µg/ml.

The following discussion is presented as a general overview of the techniques available for the production of antibodies; however, one of skill in the art will recognize that many variations upon the following methods are known.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric or humanized antibody. See, e.g., Walker et al., *Molec. Immunol.* 26:403 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, Fab', $F(ab)_2$, and Fv fragments; domain antibodies, diabodies; vaccibodies, linear antibodies; single-chain antibody molecules; and multispecific antibodies formed from antibody fragments. Such fragments can be produced by known techniques. For example, $F(ab')_2$ fragments can be produced by pepsin digestion of the antibody molecule, and Fab fragments can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 254:1275 (1989)). In some embodiments, the term "antibody fragment" as used herein may also include any protein construct that is capable of binding a target pathogen or sperm and associate with mucin to trap the target pathogen or sperm in mucus.

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Immunogens (antigens) are used to produce antibodies specifically reactive with target polypeptides. Recombinant or synthetic polypeptides and peptides, e.g., of at least 5 (e.g., at least 7 or 10) amino acids in length, or greater, are the preferred immunogens for the production of monoclonal or polyclonal antibodies. In one embodiment, an immunogenic polypeptide conjugate is also included as an immunogen. The peptides are used either in pure, partially pure or impure form. Suitable polypeptides and epitopes for target pathogens and sperm are well known in the art. Polynucleotide and polypeptide sequences are available in public sequence databases such as GENBANK®/GENPEPT®. Large numbers of neutralizing and non-neutralizing antibodies that specifically bind to target pathogens and sperm have been described in the art and can be used as starting material to prepare the antibodies of the present invention. Alternatively, new antibodies can be raised against target pathogens and sperm using the techniques described herein and well known in the art.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, e.g., a purified or synthetic peptide, a peptide coupled to an appropriate carrier (e.g., glutathione-S-transferase, keyhole limpet hemanocyanin, etc.), or a peptide incorporated into an immunization vector such as a recombinant vaccinia virus is optionally mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired. Antibodies, including binding fragments and single chain recombinant versions thereof, against the polypeptides are raised by immunizing animals, e.g., using immunogenic conjugates comprising a polypeptide covalently attached (conjugated) to a carrier protein as described above. Typically, the immunogen of interest is a polypeptide of at least about 10 amino acids, in another embodiment the polypeptide is at least about 20 amino acids in length, and in another embodiment, the fragment is at least about 30 amino acids in length. For example, the polypeptide can comprise amino acids acid residues 1 through 200 from the N-terminal of the papillomavirus L2 protein. The immunogenic conjugates are typically prepared by coupling the polypeptide to a carrier protein (e.g., as a fusion protein) or, alternatively, they are recombinantly expressed in an immunization vector.

Monoclonal antibodies are prepared from cells secreting the desired antibody. These antibodies are screened for binding to normal or modified peptides, or screened for agonistic or antagonistic activity. Specific monoclonal and polyclonal antibodies will usually bind with a $K_D$ of at least about 50 mM, e.g., at least about 1 mM, e.g., at least about 0.1 mM or better. In some instances, it is desirable to prepare monoclonal antibodies from various mammalian hosts, such as mice, rodents, primates, humans, etc. Description of techniques for preparing such monoclonal antibodies are found in Kohler and Milstein 1975 *Nature* 256:495-497. Summarized briefly, this method proceeds by injecting an animal with an immunogen, e.g., an immunogenic peptide either alone or optionally linked to a carrier protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies. Other suitable techniques involve selection of libraries of recombinant antibodies in phage or similar vectors. See, Huse et al. 1989 *Science* 246:1275-1281; and Ward et al. 1989 *Nature* 341:544-546.

Antibodies specific to the target polypeptide can also be obtained by phage display techniques known in the art.

Antibodies can sometimes be labeled by joining, either covalently or noncovalently, a substance which provides a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Such antibodies are useful for detecting or diagnosing the presence of a microbe on which an antigen is found.

Method of making antibodies with a glycosylation pattern of interest can be achieved by any method known to those or skill in the art. For example, in some embodiments, mammalian cells can be used, such as, Chinese hamster ovary (CHO) cells, baby hamster kidney (BHK) cells, and NS0- and SP2/0-mouse myeloma cells, to produce antibodies having the desired glycosylation pattern. In certain embodiments, human cell lines can be used, e.g., 293 cells. In some embodiments, non-mammalian cells can be used. The cell line can be genetically engineered to produce the antibodies with the desired oligosaccharide. Such cell lines can have altered expression, for example, of one or more enzymes affecting glycosylation patterns, e.g., glycosyltransferases. Glycosyltransferases include, without limitation, a galactosyltransferase, a fucosyltransferase, a glucosyltransferase, an N-acetylgalactosaminyltransferase, an N-acetylglucosaminyltransferase, a glucuronyltransferase, a sialyltransferase, a mannosyltransferase, a glucuronic acid transferase, a galacturonic acid transferase, an oligosaccharyltransferase, or any combination thereof. Specific examples include, without limitation, oligosaccharyltransferase, UDP-N-acetyl-D-galactosamine:polypeptide N-acetylgalactosaminyltransferase, GDP-fucose protein:O-fucosyltransferase 1, GDP-fucose protein:O-fucosyltransferase 2, protein:O-glucosyltransferase, UDP-N-acetylglucosamine:peptide N-aeetylglucosaminyltransferase, protein:O-mannosyltransferase, β1,4 galactosyltransferase, and any combination thereof. Enzymes involved in glycosylation of proteins are well known in the art and can be manipulated using routine techniques. See, for example, U.S. Pat. Nos. 8,383,106, 8,367,374, 8,080,415, 8,025,879, 8,021,856, 7,906,329, and 7,846,434, each incorporated herein by reference in its entirety. In other embodiments, glycans can be synthesized in specific patterns and linked to antibodies. In further embodiments, antibodies with mixed glycosylation patterns can be separated to isolate antibodies with the desired glycosylation pattern.

As would be recognized by one skilled in the art, the antibodies of the presently-disclosed subject matter can also be formed into suitable compositions, e.g., pharmaceutical compositions for administration to a subject in order to treat or prevent an infection caused by a target pathogen or a disease or disorder caused by infection by a target pathogen or to provide contraception. In one embodiment, the compositions comprise, consist essentially of, or consist of an antibody of the invention in a prophylactically or therapeutically effective amount and a pharmaceutically-acceptable carrier.

Pharmaceutical compositions containing the antibodies as disclosed herein can be formulated in combination with any suitable pharmaceutical vehicle, excipient or carrier that would commonly be used in this art, including such conventional materials for this purpose, e.g., saline, dextrose, water, glycerol, ethanol, and combinations thereof. As one skilled in this art would recognize, the particular vehicle, excipient or carrier used will vary depending on the subject and the subject's condition, and a variety of modes of administration would be suitable for the compositions of the invention. Suitable methods of administration of any pharmaceutical composition disclosed in this application include, but are not limited to, topical, oral, intranasal, buccal, inhalation, anal, and vaginal administration, wherein such administration achieves delivery of the antibody to a mucus membrane of interest.

The composition can be any type of composition suitable for delivering antibody to a mucosal surface and can be in various forms known in the art, including solid, semisolid, or liquid form or in lotion form, either oil-in-water or water-in-oil emulsions, in aqueous gel compositions. Compositions include, without limitation, gel, paste, suppository, douche, ovule, foam, film, spray, ointment, pessary, capsule, tablet, jelly, cream, milk, dispersion, liposomes, powder/talc or other solid, suspension, solution, emulsion, microemulsion, nanoemulsion, liquid, aerosol, microcapsules, time-release capsules, controlled release formulation, sustained release formulation or bioadhesive gel (e.g., a mucoadhesive thermogelling composition) or in other forms embedded in a matrix for the slow or controlled release of the antibody to the surface onto which it has been applied or in contact.

If topical administration is desired, the composition may be formulated as needed in a suitable form, e.g., an ointment, cream, gel, lotion, drops (such as eye drops and ear drops), or solution (such as mouthwash). The composition may contain conventional additives, such as preservatives, solvents to promote penetration, and emollients. Topical formulations may also contain conventional carriers such as cream or ointment bases, ethanol, or oleyl alcohol. Other formulations for administration, including intranasal administration, etc., are contemplated for use in connection with the presently-disclosed subject matter. All formulations, devices, and methods known to one of skill in the art which are appropriate for delivering the antibody or composition containing the antibody to one or more mucus membranes of a subject can be used in connection with the presently-disclosed subject matter.

The compositions used in the methods described herein may include other agents that do not negatively impact or otherwise affect the inhibitory and/or contraceptive effectiveness of the components of the composition, including antibodies, antimicrobial agents, and/or sperm-function inhibitors. For example, solid, liquid or a mixture of solid and liquid pharmaceutically acceptable carriers, diluents, vehicles, or excipients may be employed in the pharmaceutical compositions. Suitable physiologically acceptable, substantially inert carriers include water, a polyethylene glycol, mineral oil or petrolatum, propylene glycol, hydroxyethylcellulose, carboxymethyl cellulose, cellulosic derivatives, polycarboxylic acids, linked polyacrylic acids, such as carbopols; and other polymers such as poly(lysine), poly(glutamic acid), poly(maleic acid), polylactic acid), thermal polyaspartate, and aliphatic-aromatic resin; glycerin, starch, lactose, calcium sulphate dihydrate, terra alba, sucrose, talc, gelatin, pectin, acacia, magnesium stearate, stearic acid, syrup, peanut oil, olive oil, saline solution, and the like.

The pharmaceutical compositions described herein useful in the methods of the present invention may further include diluents, fillers, binding agents, colorants, stabilizers, perfumes, gelling agents, antioxidants, moisturizing agents, preservatives, acids, and other elements known to those skilled in the art. For example, suitable preservatives are well known in the art, and include, for example, methyl paraben, propyl paraben, butyl paraben, benzoic acid and benzyl alcohol.

For injection, the carrier will typically be a liquid, such as sterile pyrogen-free water, pyrogen-free phosphate-buffered saline solution, bacteriostatic water, or Cremophor EL® (BASF, Parsippany, N.J.). For other methods of administration, the carrier can be either solid or liquid.

For oral administration, the antibody can be administered in solid dosage forms, such as capsules, tablets, and powders, or in liquid dosage forms, such as elixirs, syrups, and suspensions. Compositions can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include tablets or lozenges comprising the antibody in a flavored base, usually sucrose and acacia or tragacanth; and pastilles comprising the antibody in an inert base such as gelatin and glycerin or sucrose and acacia. The composition can comprise an orally dissolvable or degradable composition. Alternately, the composition can comprise a powder or an aerosolized or atomized solution or suspension comprising the antibody. Such powdered, aerosolized, or atomized compositions, when dispersed, preferably have an average particle or droplet size in the range from about 0.1 to about 200 nanometers.

Compositions of the present invention suitable for parenteral administration comprise sterile aqueous and non-aqueous injection solutions of the antibody, which preparations are preferably isotonic with the blood of the intended recipient. These preparations can contain anti-oxidants, buffers, bacteriostats and solutes which render the composition isotonic with the blood of the intended recipient. Aqueous and non-aqueous sterile suspensions can include suspending agents and thickening agents. The compositions can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising an antibody, in a unit dosage form in a sealed container. The antibody is provided in the form of a lyophilizate which is capable of being reconstituted with a suitable pharmaceutically acceptable carrier to form a liquid composition suitable for injection thereof into a subject.

Compositions suitable for rectal administration are preferably presented as unit dose suppositories. These can be prepared by admixing the antibody with one or more conventional solid carriers, for example, cocoa butter, and then shaping the resulting mixture.

The antibody can alternatively be formulated for nasal administration or otherwise administered to the lungs of a subject by any suitable means, e.g., administered by an aerosol suspension of respirable particles comprising the antibody, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Harwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the antibody can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the antibody can likewise be produced with any solid particulate medicament aerosol generator, by techniques known in the pharmaceutical art.

Alternatively, one can administer the antibody in a local rather than systemic manner, for example, in a depot or sustained-release formulation.

One aspect of the invention relates to devices coated or impregnated with the antibodies and compositions of the invention. The device can be for delivery of the antibodies and compositions of the invention to a mucus membrane, e.g., to the vagina or uterus. In one embodiment, a device includes a solid support adapted to be inserted into the vagina. The support can be impregnated with or coated with a composition. The release of antibodies from the devices may be controlled by the material composing these devices, such as silicone elastomers, ethylene vinyl acetate and polyurethane polymers. Devices, such as cervicovaginal and rectal devices, include, without limitation, a ring, rod, applicator, sponge, cervical cap, tampon, diaphragm, or intrauterine device. Applicators can be those currently used commercially to deliver spermicidal gels or anti-yeast compounds and include, without limitation, plunger-type applicators, pessaries, sprays, squeezable tubes, vaginal rings, cervical rings, sponges, and the like. All such means for delivery are intended to be encompassed by the present invention.

As noted herein, antibodies of the presently-disclosed subject matter are capable of diffusing through mucus when they are unbound, to allow the antibody to bind a target pathogen or sperm at a desirable rate. It is also desirable that, when antibodies are bound to the pathogen or sperm, the cumulative effect of the antibody-mucin interactions effectively traps the pathogen or sperm in the mucus. To facilitate this goal, in some embodiments, it can be desirable to provide a composition that includes more than one antibody, wherein each antibody specifically binds a different epitope of the target pathogen or sperm. Such a composition provides the ability for an increased number of antibodies to become bound to the pathogen or sperm, thereby strengthening the antibody-mucin interactions that serve to trap the pathogen or sperm in the mucus.

In some embodiments of the presently-disclosed subject matter, a composition includes a first antibody and a second antibody, as disclosed herein, wherein the first antibody specifically binds a first epitope of the target pathogen or sperm and the second antibody specifically binds a second epitope of the target pathogen or sperm, wherein said first epitope is distinct from the second epitope. In certain embodiments, the composition includes three or more different antibodies, e.g., 3, 4, 5, 6, 7, 8, 9, 10, or more different antibodies, wherein each antibody specifically binds a different epitope of the target pathogen or sperm.

In some embodiments of the presently-disclosed subject matter, a composition includes a first antibody that specifically binds a gG surface glycoprotein of HSV, a second antibody that specifically binds a gD surface glycoprotein of HSV, and/or a third antibody that specifically binds a gB surface glycoprotein of HSV.

It is also desirable to provide a composition that can provide treatment or prevention of infection due to more than one target pathogen. In some embodiments of the presently-disclosed subject matter, a composition includes a first antibody and a second antibody, as disclosed herein, wherein the first antibody specifically binds an epitope of a first target pathogen and the second antibody specifically binds an epitope of second target pathogen. In certain embodiments, the composition includes three or more different antibodies, e.g., 3, 4, 5, 6, 7, 8, 9, 10, or more different antibodies, wherein each antibody specifically binds an epitope of a different target pathogen.

In other embodiments, a composition provides both contraception and treatment or prevention of infection by one or more target pathogens. In some embodiments of the presently-disclosed subject matter, a composition includes a first antibody and a second antibody, as disclosed herein, wherein the first antibody specifically binds an epitope of sperm and the second antibody specifically binds an epitope of a target pathogen. In certain embodiments, the composition includes three or more different antibodies, e.g., 3, 4, 5, 6, 7, 8, 9, 10, or more different antibodies, wherein one or more antibodies bind different epitopes of sperm and one or more antibodies specifically binds an epitope of a target pathogen or multiple target pathogens.

In some embodiments, the pharmaceutical composition can further include an additional active agent, e.g., a prophylactic or therapeutic agent. For example, the additional active agent can be an antimicrobial agent, as would be known to one of skill in the art. The antimicrobial agent may be active against algae, bacteria, fungi, parasites (helminths, protozoa), viruses, and subviral agents. Accordingly, the antimicrobial agent may be an antibacterial, antifungal, antiviral, antiparasitic, or antiprotozoal agent. The antimicrobial agent is preferably active against infectious diseases.

Suitable antiviral agents include, for example, virus-inactivating agents such as nonionic, anionic and cationic surfactants, and C31 G (amine oxide and alkyl betaine), polybiguanides, docosanol, acylcarnitine analogs, octyl glycerol, and antimicrobial peptides such as magainins, gramicidins, protegrins, and retrocyclins. Mild surfactants, e.g., sorbitan monolaurate, may advantageously be used as antiviral agents in the compositions described herein. Other antiviral agents that may advantageously be utilized in the compositions described herein include nucleotide or nucleoside analogs, such as tenofovir, acyclovir, amantadine, didanosine, foscarnet, ganciclovir, ribavirin, vidarabine, zalcitabine, and zidovudine. Further antiviral agents that may be used include non-nucleoside reverse transcriptase inhibitors, such as UC-781 (thiocarboxanilide), pyridinones, TIBO, nevaripine, delavirdine, calanolide A, capravirine and efavirenz. From these reverse transcriptase inhibitors, agents and their analogs that have shown poor oral bioavailability are especially suitable for administration to mucosal tissue, in combination with antibodies and compositions of the invention, to prevent sexual transmission of HIV. Other antiviral agents that may be used are those in the category of HIV entry blockers, such as cyanovirin-N, cyclodextrins, carregeenans, sulfated or sulfonated polymers, mandelic acid condensation polymers, monoclonal antibodies, chemokine receptor antagonists such as TAK-779, SCH-C/D, and AMD-3100, and fusion inhibitors such as T-20 and 1249.

Suitable antibacterial agents include antibiotics, such as aminoglycosides, cephalosporins, including first, second and third generation cephalosporins; macrolides, including erythromycins, penicillins, including natural penicillins, penicillinase-resistant penicillins, aminopenicillins, extended spectrum penicillins; sulfonamides, tetracyclines, fluoroquinolones, metronidazole and urinary tract antiseptics.

Suitable antifungal agents include amphotericin B, nystatin, griseofulvin, flucytosine, fluconazole, potassium iodide, intraconazole, clortrimazole, miconazole, ketoconazole, and tolnaftate.

Suitable antiprotozoal agents include antimalarial agents, such as chloroquine, primaquine, pyrimethamine, quinine, fansidar, and mefloquine; amebicides, such as dioloxamide, emetine, iodoquinol, metronidazole, paromomycine and quinacrine; pentamidine isethionate, atovaquone, and eflornithine.

In certain embodiments, the additional active agent can be a sperm-function inhibitor, e.g., an agent that has the ability to inhibit the function of sperm, to otherwise inhibit fertilization of an egg by sperm and/or to otherwise prevent pregnancy, such as by killing and/or functionally inactivating sperm or by other effects on the activity of the sperm. In some embodiments, the active agent may have at least dual functions, such as acting as a sperm-function inhibitor and as an antimicrobial agent.

Sperm-function inhibitors include, without limitation, surfactants, including nonionic surfactants, cationic surfactants, and anionic surfactants; spermicides, such as nonoxynol-9 ($\alpha$-(4-Nonylphenyl)-$\omega$-hydroxynona(oxyethylene); other sperm-inactivators such as sulfated or sulfonated polymers such as polystyrene sulfonate, mandelic acid condensation polymers, cyclodextrins; antimicrobial peptides such as gramicidins, magainins, indolicidin, and melittin; and acid-buffering compositions, such as BufferGel and Acid-Form. Nonionic surfactants include, for example, sorbitan monolaurate, nonylphenoxypolyethoxy ethanol, p-diisobutyphenoxypolyethoxy ethanol, polyoxyethylene (10) oleyl ether and onyx-ol. Suitable anionic surfactants include, without limitation, sodium alkyl sulfonates and the sodium alkylbenzene sulfonates. Cationic surfactants include, for example, the quaternary ammonium surfactants, such as cetyl pyrimidinium chloride and benzalkonium chlorides. Zwitterionic surfactants such as acylcarnitine analogs and C31G are especially suitable for their mild skin and mucosal irritation properties.

The presently-disclosed subject matter further includes a kit, including the antibody or composition comprising the antibody as described herein; and optionally a device for administering the antibody or composition. In some embodiments, the kit can include multiple antibodies and/or compositions containing such antibodies. In some embodiments, each of multiple antibodies provided in such a kit can specifically bind to a different epitope of the target pathogen or sperm. In other embodiments, each of multiple antibodies provided in such a kit can specifically bind to an epitope of a different target pathogen or to and epitope of sperm. In some embodiments, the kit can further include an additional active agent, e.g., antimicrobial, such as an antibiotic, an antiviral, or other antimicrobial, or a sperm-function inhibitor as would be known to one of skill in the art.

III. Prevention and Treatment of Infection

The presently-disclosed subject matter further includes methods of inhibiting or treating an infection by a target pathogen in a subject, including administering to a mucosa of the subject an antibody and/or composition as disclosed herein. The mucosa can be selected from, for example, a respiratory tract mucosa (e.g., a nasal mucosa, a lung mucosa), a reproductive tract mucosa (e.g., a genital mucosa, an uterine mucosa, a vaginal mucosa), an ocular mucosa, and a gastrointestinal mucosa (e.g., an oral mucosa, an anal mucosa), and any combination thereof. In certain embodiments, the methods comprise additional steps such as one or more of isolating the antibodies, preparing a composition of the isolated antibodies, determining the level of antibodies in the mucus of the subject before administering the antibodies, and determining the level of antibodies in the mucus of the subject after administering the antibodies.

The antibodies and compositions of the present invention according to the methods described herein are administered or otherwise applied by delivering the composition, typically to a site of infection. The site of infection may be one where an infection is already present (an actual site of infection) or where an infection is likely to occur (a potential site of site of infection in or on an uninfected individual). In some embodiments, the antibodies and compositions may be topically delivered. In other embodiments, the antibodies and compositions may be systemically delivered such that the antibodies are secreted into the mucus of the subject. Accordingly, the compositions as described above may be delivered to a mucosal surface, e.g., to the reproductive tract, e.g., to the vulva, including the vaginal cavity, and/or to the gastrointestinal tract, e.g., the ano-rectal and buccal cavities and/or to the respiratory tract, e.g., the nasal cavity and the lungs. In the vaginal cavity, the compositions may be applied to any portion of the uterus, including inside the uterus and on the cervix, including the mucosa and/or lining of the endo- and ecto-cervix. The ano-rectal cavity includes the perianal surface and the lining of the anus. Topical delivery to the gastrointestinal tract includes oral administration such that the antibodies reach, e.g., the small and/or large intestines. For example, oral administration of an enteric-coated solid oral dosage form (e.g., tablet or capsule) can effectively carry the antibodies through the stomach unharmed with release occurring in the intestines.

An effective amount of the antibody can be administered. As used herein, an "effective amount" of the antibody for inhibition of infection refers to a dosage sufficient to inhibit infection by the target pathogen. As used herein, an "effective amount" of the antibody for treatment of infection refers to a dosage sufficient to inhibit spread of the target pathogen from infected cells to non-infected cells in the subject and/or to inhibit spread of the target pathogen from the infected subject to another subject, e.g., an infected non-infected subject. The effective amount can be an amount sufficient to trap an amount of the target pathogen in mucus. As will be recognized by one of skill in the art, the amount can vary depending on the patient and the target pathogen. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of the antibody that specifically binds the target pathogen or sperm can be an amount that achieves a concentration of the antibody in the mucus of about 0.1 µg/mL to about 1000 µg/mL, e.g., about 0.5 µg/mL to about 100 µg/mL, e.g., about 1 µg/mL to about 50 µg/mL or any range therein. In some embodiments, the antibody may be administered in two or more stages with different doses in each stage. For example, higher doses can be administered initially in order to clear target pathogens that are present in the mucus of exposed or infected subjects and ensure that sufficient amounts of antibody remain in the mucus to provide protection, e.g., for about 24 hours. In later stages, lower doses can be administered to maintain protective levels of the antibody. In other embodiments, protective doses can be administered to subjects that are likely to be exposed to a pathogen and higher doses can be administered if infection occurs.

As will be recognized by one of skill in the art, the term "inhibiting" or "inhibition" does not refer to the ability to completely eliminate the possibility of infection in all cases. Rather, the skilled artisan will understand that the term "inhibiting" refers to reducing the chances of pathogens moving through mucus beyond the mucus membrane such that infection of a subject can occur, such as reducing chances of infection by a pathogen when such pathogen is bound to trapping antibodies in mucus. Such decrease in infection potential can be determined relative to a control that has not been administered the antibodies of the invention. In some embodiments, the decrease of inhibition relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments inhibiting or treating an infection in a subject can comprise trapping a pathogen in mucus. As such, in some embodiments a method of trapping a target pathogen in mucus is provided, which method includes administering to a mucosa of the subject an antibody or composition as described herein.

In some embodiments, a method of inhibiting or treating an infection in a subject, and/or trapping a pathogen in the mucus of a subject, involves administering to a mucosa of the subject a composition comprising an isolated antibody that specifically binds a non-neutralizing epitope of a target pathogen. The antibody can be a non-neutralizing antibody. In some embodiments, the non-neutralizing antibody is provided at a concentration above a predetermined amount.

In some embodiments, a method of inhibiting or treating an infection in a subject, and/or trapping a pathogen in the mucus of a subject, involves administering to a mucosa of the subject a composition comprising an isolated antibody that specifically binds a neutralizing epitope of a target pathogen, wherein the antibody is provided at a sub-neutralization dose.

As used herein, the term "subject" refers to humans and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

A subject in need of inhibiting an infection or a disease or disorder caused by an infection is a subject that has been identified as being at risk of infection. In some embodiments, the subject is identified as having been exposed to the target pathogen. In other embodiments, the subject is in contact with other subjects that are infected or are likely to become infected, e.g., a subject that is living with, working with, and/or attending school with infected subjects.

A subject in need of treating an infection or a disease or disorder caused by an infection is a subject that has been diagnosed as infected with a pathogen or is suspected of being infected with a pathogen, e.g., exhibiting symptoms of infection.

In particular embodiments of the invention, more than one administration (e.g., two, three, four, or more administrations) of the antibody, composition, or device comprising the composition can be employed over a variety of time intervals (e.g., hourly, daily, weekly, monthly, etc.) to achieve prophylactic and/or therapeutic effects.

In some embodiments, the method include administering an antibody, and further administering an additional active agent, e.g., prophylactic or therapeutic agent, e.g., an antimicrobial, such as an antibiotic, an antiviral, or other antimicrobial as would be known to one of skill in the art. The additional active agents can be delivered concurrently with the antibodies and compositions of the invention. The additional active agents can be delivered in the same composition as the antibody or in separate compositions. As used herein, the word "concurrently" means sufficiently close in time to produce a combined effect (that is, concurrently can be simultaneously, or it can be two or more events occurring within a short time period before or after each other).

IV. Contraception

One aspect of the invention relates to methods of contraception. One embodiment relates to a method of providing contraception, e.g., inhibiting fertilization, in a female subject, comprising administering to the mucosa of the reproductive tract, e.g., the vaginal and/or cervical mucosa, of the subject an antibody or composition of the invention in an amount effective to inhibit sperm-egg fertilization, and thus prevent pregnancy. In an additional embodiment, the method can be practiced on a male subject to trap sperm in the epydidimal mucus. In certain embodiments, the methods comprise additional steps such as one or more of isolating the antibodies, preparing a composition of the isolated antibodies, determining the level of antibodies in the mucus of the subject before administering the antibodies, and determining the level of antibodies in the mucus of the subject after administering the antibodies.

The antibodies and compositions of the present invention according to the methods described herein are administered or otherwise applied by delivering the composition, typically to the reproductive tract. In some embodiments, the antibodies and compositions may be topically delivered. In other embodiments, the antibodies and compositions may be systemically delivered such that the antibodies are secreted into the mucus of the subject. Accordingly, the compositions as described above may be delivered to a mucosal surface of the reproductive tract, e.g., to the vulva, including the vaginal cavity. In the vaginal cavity, the compositions may be applied to any portion of the uterus, including inside the uterus and on the cervix, including the mucosa and/or lining of the endo- and ecto-cervix.

An effective amount of the antibody can be administered. As used herein, an "effective amount" of the antibody for contraception refers to a dosage sufficient to inhibit sperm from contacting an egg and fertilizing it. The effective amount can be an amount sufficient to trap an amount of the sperm in mucus. As will be recognized by one of skill in the art, the amount can vary depending on the subject. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of antibody can be an amount that achieves a concentration of antibody in the mucus of about 0.1 µg/mL to about 1000 µg/mL, e.g., about 0.5 µg/mL to about 100 µg/mL, e.g., about 1 µg/mL to about 50 µg/mL or any range therein.

As will be recognized by one of skill in the art, the term "inhibiting" or "inhibition" does not refer to the ability to completely eliminate the possibility of fertilization in all cases. Rather, the skilled artisan will understand that the term "inhibiting" refers to reducing the chances of sperm moving through mucus beyond the mucus membrane such that fertilization of a subject can occur, such as reducing chances of fertilization by a sperm when such sperm is bound to trapping antibodies in mucus. Such decrease in fertilization potential can be determined relative to a control that has not been administered the antibodies of the invention. In some embodiments, the decrease of fertilization relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments providing contraception in a subject can comprise trapping sperm in mucus. As such, in some embodiments a method of trapping sperm in mucus is provided, which method includes administering to a mucosa in the reproductive tract of the subject an antibody or composition as described herein.

As used herein, the term "subject" refers to humans and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

In particular embodiments of the invention, more than one administration (e.g., two, three, four, or more administrations) of the antibody, composition, or device comprising the composition can be employed over a variety of time intervals (e.g., hourly, daily, weekly, monthly, etc.) to achieve prophylactic/contraceptive effects. In some embodiments, the antibody, composition, or device is administered regularly or constantly. In other embodiments, the antibody, composition, or device is administered on an as needed basis, e.g., prior to sexual activity and/or following sexual activity.

In some embodiments, the method include administering an antibody, and further administering an additional active agent, e.g., prophylactic or therapeutic agent, e.g., a sperm-function inhibitor and/or an antimicrobial, such as an antibiotic, an antiviral, or other antimicrobial as would be known to one of skill in the art. The additional active agents can be delivered concurrently with the antibodies and compositions of the invention. The additional active agents can be delivered in the same composition as the antibody or in separate compositions. As used herein, the word "concurrently" means sufficiently close in time to produce a combined effect (that is, concurrently can be simultaneously, or it can be two or more events occurring within a short time period before or after each other).

V. Monitoring Vaccine Effectiveness

Having discovered the usefulness of the antibodies of the invention in preventing and treating infection by pathogens and/or diseases or disorders caused by infection by pathogens, another aspect of the invention relates to detecting the presence of such antibodies in a subject in order to determine how well the subject is protected against possible infection. For example, a subject that has been vaccinated against a particular pathogen can be monitored for the presence and level of antibodies that have trapping potency in mucus or other body fluids, e.g., saliva. If such antibodies do not appear in the mucus or appear at non-prophylactic or non-therapeutic levels, the subject can be administered a booster vaccination and/or a different vaccine in order to generate an effective amount of antibodies. For example, subjects can be monitored to ensure a level of antibodies in mucus that at least equal to the level of antibodies observed in a subject that has been exposed previously to a pathogen.

Thus, one embodiment relates to a method of monitoring the effectiveness of a vaccination in a subject that has been vaccinated against a target pathogen, comprising determining in a mucus sample from said subject the amount of an antibody comprising an oligosaccharide at a glycosylation site, the oligosaccharide having a glycosylation pattern that enhances trapping potency of the antibody in mucus, wherein the antibody specifically binds an epitope of said target pathogen, wherein the amount of said antibody is indicative of the effectiveness of the vaccination.

The mucus to be sampled can be from the appropriate mucosal surface where the antibody is expected to be found. Samples of mucus can be obtained from a subject by methods routinely used in the art. Similarly, samples of other body fluids such as saliva can be obtained from a subject by methods routinely used in the art.

A variety of assays can be employed for detection and/or quantitation of the antibody. For example, various immunoassays can be used to detect antibodies of this invention. Such immunoassays typically involve the measurement of antigen/antibody complex formation between a protein or peptide (i.e., an antigen) and its specific antibody.

The immunoassays of the invention can be either competitive or noncompetitive and both types of assays are well-known and well-developed in the art. In competitive binding assays, antigen or antibody competes with a detectably labeled antigen or antibody for specific binding to a capture site bound to a solid surface. The concentration of labeled antigen or antibody bound to the capture agent is inversely proportional to the amount of free antigen or antibody present in the sample.

Noncompetitive assays of this invention can be, for example, sandwich assays, in which, for example, the antigen is bound between two antibodies. One of the antibodies is used as a capture agent and is bound to a solid surface. The other antibody is labeled and is used to measure or detect the resultant antigen/antibody complex by e.g., visual or instrument means. A number of combinations of antibody and labeled antibody can be used, as are well known in the art. In some embodiments, the antigen/antibody complex can be detected by other proteins capable of specifically binding human immunoglobulin constant regions, such as protein A, protein L or protein G. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401 (1973); Akerstrom et al., *J. Immunol.*, 135:2589 (1985)).

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., 35S, $^{125}$I, $^{32}$P, $^{3}$H, $^{14}$C, $^{131}$I), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, immunoprecipitation, competitive binding assays and immunohistochemical staining. These and other assays are described, among other places, in Hampton et al. (*Serological Methods, a Laboratory Manual*, APS Press, St Paul, Mimi (1990)) and Maddox et al. (*J. Exp. Med.* 158:1211 (1993); the entire contents of which are incorporated herein by reference for teachings directed to immunoassays).

The methods of this invention can also be carried out using a variety of solid phase systems, such as described in U.S. Pat. No. 5,879,881, as well as in a dry strip lateral flow system (e.g., a "dipstick" system), such as described, for example, in U.S. Patent Publication No. 2003/0073147, the entire contents of each of which are incorporated by reference herein.

The detection and/or quantitation of the antibody in the mucus sample can further comprise characterization of the glycosylation pattern of the antibody. Determination of the glycosylation pattern can be carried out using methods well known in the art and described herein, including glycan sequencing and separation techniques such as gel electrophoresis, fluorescence-activated sorting, and mass spectrometry.

Having described the present invention, the same will be explained in greater detail in the following examples, which are included herein for illustration purposes only, and which are not intended to be limiting to the invention.

Example 1

Materials and Methods

Culture and Purification of Fluorescent HSV-1:

The HSV-1 mutant 166v (Elliott et al., *J. Virol.* 73:4110 (1999)), encoding a VP22-Green Fluorescent Protein (GFP) tegument protein packaged into HSV-1 at relatively high copy numbers (Heine et al., *J. Virol.* 14:640 (1974)), was kindly provided by Richard Courtney and used in all microscopy and ELISA studies, besides those for in vivo experiments. The addition of GFP to the VP22 protein appears to have no deleterious effects on viral replication (Elliott et al., *J. Virol.* 73:4110 (1999)), and the fluorescence of 166v was consistently more intense than that of HSV-1 mutants encoding other GFP fusion proteins. 166v was expanded at an MOI of 3 on confluent monolayers of HaCat cells maintained in DMEM (Life Technologies, Grand Island, N.Y.) supplemented with 5% FBS, 1× L-glutamine and 1× Penicillin/Streptomycin. Culture medium was collected 16-18 hr post-infection and twice centrifuged at 1000×g for 5 min to remove cell debris. The resulting supernatant was split into 30 mL aliquots and precipitated overnight with a polyethylene glycol (PEG)/salt solution. Briefly, 10 mL of 1.55 M NaCl was added to 30 mL of crude virus supernatant, followed by 10 mL of 40% PEG 8000 (Sigma, St. Louis, Mo.). After an overnight incubation at 4° C. the virus/PEG solution was centrifuged at 2555×g and 4° C. for 1 hr. The virus pellet was then resuspended in 1×PBS and centrifuged through a continuous 20-50% (w/w) sucrose in PBS gradient for 1 hr at 74,119×g. The resulting virus band was collected, diluted 1:5 in PBS, layered over 30% (w/w) sucrose in PBS, and centrifuged for 1.5 hr at 83,472×g to pellet virus for further purification. Purified virus pellet was resuspended in PBS and stored as single use aliquots at −80° C.

Cervicovaginal Mucus (CVM) Collection and Characterization:

CVM collection was performed as published previously (Lai et al., *J. Virol.* 83:11196 (2009); Lai et al., *Proc. Natl. Acad. Sci. U.S.A.* 107:598 (2010)). Briefly, undiluted CVM secretions, averaging 0.3 g per sample, were obtained from women of reproductive age, ranging from 20 to 32 years old (27.4±0.9 years, mean±SEM), by using a self-sampling menstrual collection device following protocols approved by the Institutional Review Board of the University of North Carolina—Chapel Hill. Informed consent of participants was obtained after the nature and possible consequences of the study were explained. Participants inserted the device into the vagina for at least 30 s, removed it, and placed it into a 50 mL centrifuge tube. Samples were centrifuged at 230×g for 2 min to collect the secretions. Aliquots of CVM for lactic acid and Ab measurements (diluted 1:5 with 1×PBS and stored at −80° C.) and slides for gram staining were prepared immediately, and the remainder of the sample was stored at 4° C. until microscopy, typically within a few hours. Samples were collected at random times throughout the menstrual cycle, and cycle phase was estimated based on the last menstrual period date normalized to a 28 day cycle. No samples were ovulatory based on visual observation (none exhibited spinnbarkeit). Samples that were non-uniform in color or consistency were discarded. Donors stated they had not used vaginal products nor participated in unprotected intercourse within 3 days prior to donating. All samples had pH<4.5; none had bacterial vaginosis (BY) based on Gram staining and Nugent scoring, following scoring criteria described previously (Nugent et al., *J. Clin. Microbiol.* 29:297 (1991)). For lactic acid and Ab measurements, CVM aliquots were thawed and centrifuged for 2 min at 21,130×g to obtain cell-free supernatant containing lactic acid and Ab. Lactic acid content was measured using a DA-lactic acid kit (R-Biopharm, Darmstadt, Germany) according to manufacturer protocol, but adapted to a 96-well format.

Total immunoglobulin levels in CVM were quantified using the Human Isotyping Kit (HGAMMAG-301K; Millipore, Billerica, Mass.) according to manufacturer protocol. Briefly, 20× stock isotyping beads were vortexed, sonicated, diluted to IX, and incubated with 50 µL of serially diluted CVM supernatant at 1:2 beads:CVM volume ratio. After 1 hr, the beads were separated from CVM supernatant using a magnetic plate, and washed twice with wash buffer. The beads were then incubated with 25 µL of 1× anti-Human Kappa and Lambda-PE for 1 hr, washed twice, and resuspended in Luminex Drive fluid. Fluorescence intensities indicative of immunoglobulin levels present in CVM were measured using the Luminex MAGPIX system, and data analysis was performed using Milliplex Analyst (v3.5.5.0; Vigene Tech Inc., Carlisle, Mass.). All incubations were carried out at room temperature in the dark with vigorous agitation.

Whole-virus ELISA was used to quantify HSV-1 specific IgG. Briefly, high-affinity 96-well half-area plates (Thermo Scientific, Rockford, Ill.) were coated overnight at 4° C. with 25 µL per well of affinity-purified intact HSV-1 at 20 µg/mL (measured using BCA assay). The plates were washed four times with 0.05% Tween in PBS (PBS-T), blocked with 5% milk for at least 1 hr followed by PBS-T washes, then incubated for at least 1 hr with serial dilutions of CVM supernatant. Following PBS-T washes, virion-bound IgG was quantified using F(ab')$_2$ anti-human IgG Fc (Goat)-HRP conjugate (709-1317; Rockland, Gilbertsville, Pa.) and 1-Step Ultra TMB substrate (Thermo Scientific, Rockford, Ill.), and compared to a standard generated on the same plate using twice-purified anti-HSV-1 IgG, which was assumed to be >90% pure. TMB conversion was terminated with 2 N sulfuric acid, and absorbance was measured at 450 nm using a BioTek Synergy 2 plate reader. HSV-1 specific IgA and IgM levels were too low to be detected by this assay.

Preparation and Characterization of Anti-HSV-1 IgG:

Anti-HSV-1 IgG was purified from intravenous immunoglobulin (IVIg, Privigen®; ≥98% IgG; CSL Behring, King of Prussia, Pa.) by affinity column purification. Briefly, HSV glycoproteins were extracted from purified HSV-1 by overnight incubation with Triton X-100 (final concentration 0.05%) at 4° C., followed by centrifugation at 21,130×g and 4° C. for 1.5 hr. The resulting supernatant containing HSV glycoproteins was coupled to AminoLink Plus Coupling Resins (Thermo Scientific, Rockford, Ill.) according to manufacturer protocol, and stored at 4° C. until use. To extract HSV-1 specific IgG, the column was first warmed to room temperature and washed twice with 3 mL of equilibrium buffer (150 mM NaCl, 0.05% Tween, 10 mM sodium phosphate at pH 6). The column was then loaded with 2 mL of IVIg buffer exchanged into equilibrium buffer using a 50 kDa MWCO concentrator (Corning, Tewksbury, Mass.), and incubated at room temperature for at least 45 min with end-over-end mixing. Unbound, non-specific Ab was removed by washing with 1 mL of equilibrium buffer followed by three additional rounds of wash buffer (4 mL each round; 500 mM NaCl, 0.05% Tween, 10 mM sodium phosphate at pH 6). Bound Ab was then eluted using IgG Elution Buffer (Thermo Scientific, Rockford, Ill.); each elution consisted of three 3 mL volumes of elution buffer, and was collected into tubes containing 100 µL of 10 mM sodium phosphate pH 6 to neutralize the elutions. Elutions from multiple runs were pooled together, concentrated and buffer exchanged into PBS using a 30 kDa MWCO concentrator tube, supplemented with sodium azide (final concentration 0.03%) and stored at 4° C. until use. A single purification round removed over 99% of non-specific IgG, tested by spiking IVIg with mouse IgG. Final concentration of purified IgG was measured via sandwich ELISA, with plates coated with 2 µg/mL of anti-human IgG Fc (Alpha Diagnostics, San Antonio, Tex.) followed by detection with F(ab')$_2$ anti-human IgG Fc (Goat)-HRP, and compared to a standard curve generated with serial dilutions of stock IVIg.

Preparation and Characterization of Anti-HSV-1 F(Ab')$_2$:

HSV-1 specific IgG was fragmented using a F(ab')$_2$ Preparation Kit (Thermo Scientific, Rockford, Ill.). Briefly, IgG was desalted into IgG Digestion Buffer using 3 kDa MWCO concentrator tubes (Amicon 0.5 mL; Millipore, Billerica, Mass.) and incubated with pepsin at 37° C. for 3.5 hr with end-over-end mixing, followed by purification using a Protein A column (0.2 mL resin; Thermo Scientific, Rockford, Ill.) and PBS washes to remove undigested IgG. Fragmentation was confirmed using a non-reducing 4-12% Bis-Tris gel with MOPS running buffer. The gel was stained with Coomassie Blue for imaging; note that the gel image presented in FIG. 3 was desaturated and contrast-adjusted using Pixlr photo editor to produce a black and white image (same settings applied across entire image). A competitive inhibition ELISA was also performed to confirm that the purified F(ab')$_2$ blocked binding of intact anti-HSV-1 IgG. HSV-1 coated wells were incubated with either 1% milk or different dilutions of anti-HSV-1 F(ab')$_2$ for 1 hr, followed by incubation with intact HSV-1 specific IgG for 1 hr and quantification of bound IgG using F(ab)$_2$ anti-human IgG Fc (Goat)-HRP conjugate. Total amounts of anti-HSV-1 F(ab')$_2$ were quantified via sandwich ELISA with plates coated with HSV-1 virions as described above, but with detection by anti-human IgG F(ab')$_2$ (Goat)-HRP conjugate (Rockland 209-1304).

Preparation and Characterization of Deglycosylated Anti-HSV-1 IgG:

N-linked oligosaccharides on purified anti-HSV-1 IgG were cleaved by incubating 200 µg of IgG with 10 µL of PNGase and 11 µL of 10×G7 reaction buffer (New England Biolabs, Ipswich, Mass.) for at least 24 hr at 37° C. IgG was then recovered using a Protein A column, eluted with IgG Elution Buffer into 100 µL of 10 mM sodium phosphate pH 6 and buffer exchanged into PBS using a 30 kDa MWCO concentrator tube. The deglycosylated IgG was further purified using a 0.8 mL spin column immobilized with Con A-agarose slurry (Vector Labs, Burlingame, Calif.) and washed thrice with equilibrium buffer (10 mM HEPES with 0.15 M NaCl at pH 7.5) prior to incubation with end-over-end mixing for 45 min at room temperature. Following the incubation, the column was spun at 5000×g for 1 min to collect the flow through, which contains the deglycosylated IgG, and washed thrice with equilibrium buffer to maximize recovery. The flow through and the washes were pooled, buffer exchanged into PBS using a 30 kDa MWCO concentrator tube, supplemented with sodium azide (final concentration 0.03%) and stored at 4° C. until use. Total amounts of deglycosylated IgG were measured as described above. Deglycosylation was confirmed using a lectin-ELISA assay. Briefly, high-affinity 96-well plates were coated overnight at 4° C. with 50 µL per well of 1 µg/mL purified deglycosylated HSV-1 IgG. The plates were washed 4× with PBS-T, blocked with 300 µL/well of 1× Carbo Free solution (Vector Labs, Burlingame, Calif.) for at least 1 hr followed by PBS-T washes, then incubated with 50 µL/well of 1 µg/mL biotinylated Con A lectin (Vector Labs, Burlingame, Calif.) for at least 2 hr. Following PBS-T washes, IgG-bound lectin was quantified using anti-biotin-HRP conjugate (Vector Labs, Burlingame, Calif.) and 1-Step Ultra TMB substrate, and compared to wells coated with affinity-purified HSV-1 IgG or IVIg. TMB conversion was terminated with 2 N sulfuric acid, and absorbance was measured at 460 nm using a BioTek Synergy 2plate reader and normalized to the amount of IgG bound to coated wells quantified using F(ab')$_2$ anti-human IgG Fc (Goat)-HRP conjugate.

Neutralization Assay:

Purified HSV-1 (~550 PFU; 5 µL) was incubated with 95 µL of HSV-1 specific IgG solution at different final concentrations for 1 hr with end-over-end mixing. The mixture was then diluted with 210 µL of media, of which duplicate 150 µL aliquots were transferred to confluent Vero cell monolayers in a 6-well plate. Plates were incubated at 37° C. for 1 hr with periodic rocking to ensure that the plates did not dry out, before the HSV-1/Ab mixture was aspirated off and wells were washed with 2 mL of PBS. The plates were then incubated for 3 days at 37° C. in 2% carboxymethyl cellulose in EMEM supplemented with 1× L-glutamine and 1× Penicillin/Streptomycin, before staining with 1% crystal violet solution, and the resulting plaques were manually counted and compared to control wells to determine the extent of neutralization.

Multiple Particle Tracking of HSV-1 in CVM:

To mimic neutralization of CVM by alkaline seminal fluid, we titrated CVM to pH 6.8-7.1 using small volumes (~3% v/v) of 3 N NaOH, and confirmed pH using a micro pH electrode (Microelectrodes, Inc., Bedford, N.H.) calibrated to pH 4, 7 and 10 buffers. Samples were either untreated or treated by addition of known amounts of purified anti-HSV-1 IgG or control (anti-biotin) IgG. Control beads consisted of red or green fluorescent 200 nm carboxyl-modified polystyrene particles (Molecular Probes, Eugene, Oreg.), either uncoated (PS; muco-adhesive) or covalently conjugated with low molecular weight (2 kDa), amine-functionalized polyethylene glycol (PEG; Rapp Polymere, Tuebingen, Germany) to produce coated particles (PS-PEG; muco-inert), as previously described (Lai et al., *Proc. Natl. Acad. Sci. U.S.A.* 104:1482 (2007)). Fluorescent virions or control beads (approximately $10^8$-$10^9$ particles/mL) were added at 5% v/v to 20 µL of CVM placed in a custom-made glass chamber, and incubated for 1 hr at 37° C. prior to microscopy. The translational motions of the particles were recorded using an EMCCD camera (Evolve 512; Photometrics, Tucson, Ariz.) mounted on an inverted epifluorescence microscope (AxioObserver D1; Zeiss, Thornwood, N.Y.), equipped with an Alpha Plan-Apo 100×/1.46 NA objective, environmental (temperature and $CO_2$) control chamber and an LED light source (Lumencor Light Engine DAPI/GFP/543/623/690). Videos (512×512, 16-bit image depth) were captured with MetaMorph imaging software (Molecular Devices, Sunnyvale, Calif.) at a temporal resolution of 66.7 ms and spatial resolution of 10 nm (nominal pixel resolution 0.156 µm/pixel) for 20 s. The tracking resolution was determined by tracking the displacements of particles immobilized with a strong adhesive, following a previously described method (Apgar et al., *Biophys. J.* 79:1095 (2000)). Particle trajectories were analyzed using MetaMorph software as described previously (Lai et al., *Proc. Natl. Acad. Sci. U.S.A.* 104:1482 (2007); Lai et al., *J Virol.* 83:11196 (2009); Lai et al., *Proc. Natl. Acad. Sci. U.S.A.* 107:598 (2010)); image contrast was adjusted to improve particle visibility, but the same contrast level was applied throughout the entire video and did not bias toward any particle population. Sub-pixel tracking resolution is obtained by determining the precise location of the particle centroid by light-intensity-weighted averaging of neighboring pixels. Trapped particles were defined as those with effective diffusivity ($D_{eff}$)<0.01 µm$^2$/s at a time scale (t) of 1 s (i.e., particles move less than their diameter within 1 s). In a subset of experiments, it was confirmed that particles defined as trapped over the course of 20 s based on this criterion remain confined to the same locations over more than 15 min. The slope a of the log-log mean square displacement (<MSD>) vs. time scale plot provides a further measure of particle mobility: $\alpha=1$ for pure unobstructed Brownian diffusion, e.g., particles in water, a becomes smaller as obstruction to particle diffusion increases, and $\alpha$ is zero for permanently trapped particles. At least five independent experiments in CVM from different donors, with n≥100 particles per experiment, were performed for each condition. For a subset of donors, similar observations were made at least twice in samples obtained on separate days to ensure reproducibility, but only one sample was used for analysis.

Mouse Vaginal HSV-2 Challenge Model:

All experiments conducted with mice were performed in accordance with protocols approved by the Johns Hopkins University Animal Care and Use Committee satisfying the requirements of the E.E.C. Guidelines (1986) and U.S. Federal Guidelines (1985). Female CF-1 mice (6-8 weeks old; Harlan, Frederick, Md.) were treated with Depo-Provera® (medroxyprogesterone acetate, 2.5 mg/mouse) by subcutaneous injection into the right flank 6-8 days prior to use, Depo-Provera® synchronizes mice in a prolonged diestrus-like state, in which the vaginal epithelium thins and susceptibility of the tissue to infection increases (Cone et al., *BMC Infect. Dis.* 6:90 (2006)). Depo-Provera®-treated mice were randomly divided into groups of ten. The mouse vagina is pH neutral (Meysick et al., *J. Parasitol.* 78:157 (1992)); therefore, no attempt was made to modify vaginal pH prior to inoculation. Inocula were prepared by mixing HSV-2 (final dose 2 ID$_{50}$; strain G, ATCC, Manassas, Va.) with medium or different concentrations of control (anti-biotin) or anti-gG IgG (8.F.141; Santa Cruz Biotechnology, Inc., Santa Cruz, Calif.), and incubating for 1 hr at 37° C. Mice were inoculated with 20 µL of HSV-2 solution, delivered to the vagina using a 50 µL Wiretrol (Drummond, Broomall, Pa.), fire-polished to avoid damage to the vaginal epithelium. In some studies, the mouse vagina was gently washed with ~10 mL of normal saline delivered at 1 mL/min through a smooth ball-tipped gavage needle connected to a syringe pump, prior to HSV-2 challenge. Removal of mucus by this process was measured using a fluorimetrie mucin assay, as previously described (Crowther et al., *Anal. Biochem.* 163:170 (1987)). Importantly, the gentle wash did not damage the vaginal epithelium, as confirmed by microscopy with a fluorescence-based dead cell stain (YOYO-1) that assesses membrane integrity (Cone et al., 2006), compared to conventional lavage and/or vaginal swabbing with a cotton tip, which induced significant epithelial damage. YOYO-1 has been previously used to reveal toxicity caused by detergent-based microbicides that led to increased susceptibility to HSV infection (Cone et al., *BMC Infect. Dis.* 6:90 (2006)). Tissue sectioning and H&E staining was performed by the Animal Histopathology lab at the University of North Carolina—Chapel Hill. Infection was assayed three days post-inoculation by detection of virus in vaginal lavages. Briefly, 50 µL of medium was pipetted in and out of the vagina 20 times, diluted to 0.2 mL and placed on target cells (ELVIS® HSV Test System; Diagnostic Hybrids, Athens, Ohio); infected cells (foci) were identified one day later, following manufacturer protocol. Scores for virus shedding were assigned on a scale of 0-4 based on the approximate density of foci observed ("0": 0; "0.5": <100; "1": 100-500; "2": 500-1000; "3": 1000+; "4"; saturated). At least three independent experiments were performed for each condition, with n=10 animals per experimental group (n≥30 total).

Statistical Analysis:

Correlation between endogenous anti-HSV-1 IgG levels and average particle or virus $D_{eff}$ in individual CVM samples was measured using Pearson's correlation coefficient (r). Statistical comparisons were limited to two groups (test group compared with the appropriate control group performed during the same experiment). Fisher's exact test was used to determine the statistical significance of reductions in % mice infected. A two-tailed Student's t-test (paired for comparisons of Ab-treated vs, native CVM for the same CVM samples) was used for all other comparisons. Differences were deemed significant at an alpha level of 0.05. All values are reported as mean±SEM unless otherwise indicated.

Example 2

Trapping of HSV in Cervicovaginal Mucus

The hypothesis of trapping-in-mucus was explored using HSV-1 (d~180 nm), a highly prevalent sexually transmitted virus. Fresh, undiluted CVM was obtained predominantly from donors with normal *lactobacillus*-dominated vaginal microbiota, as confirmed by Nugent scoring (Table 1). HSV-1 virions expressing a VP22-GFP tegument protein construct, packaged at high copy numbers while maintaining native viral envelope integrity, were mixed into CVM pHneutralized to mimic neutralization by alkaline seminal fluid. Time-lapse microscopy of virion motions in real-time was then performed with high spatiotemporal resolution, and virion mobility was quantified using multiple particle tracking over a long time scale. Substantial differences in HSV-1 mobility were observed in CVM samples from different donors (FIG. 1A) in 7 of 12 CVM samples, most virions diffused distances spanning several microns over the course of 20 s, whereas in the remaining 5 CVM samples, the majority of virions were essentially trapped, moving less than their diameter (<200 nm) in 20 s.

TABLE 1

Characterization of CVM samples: menstrual cycle phase, Nugent score and % lactic acid.

| Donor ID | Cycle day[1] | Cycle phase[3] | Nugent score[4] | % Lactic acid[5] |
|---|---|---|---|---|
| F10 | 17 | Luteal | 1 | 2.4 ± 0.039 |
| F12 | 25 | Luteal | 2 | 0.81 ± 0.081 |
| F14 | 26 | Luteal | 2 | 0.95 ± 0.10 |
| F18 | 11 | Follicular | 4 | 0.56 ± 0.022 |
| F9 | N/A[2] | N/A | 0 | 0.93 ± 0.062 |
| F13 | 9 | Follicular | 0 | 1.1 ± 0.031 |
| F15 | 25 | Luteal | 0 | 1.1 ± 0.042 |
| F17 | N/A | N/A | 1 | 1.2 ± 0.088 |
| F2 | 15 | Luteal | 2 | 0.74 ± 0.073 |
| F21 | N/A | N/A | 0 | 1.5 ± 0.081 |
| F5 | 10 | Follicular | 0 | 1.4 ± 0.074 |
| F8 | 19 | Luteal | 0 | 1.9 ± 0.15 |
| | | Median | 0.5 | 1.10 |
| | | SEM | 0.37 | 0.15 |

[1]Cycle day calculated as the number of days from the first day of the last menstrual period normalized by the cycle length to a 28 day cycle.
[2]N/A = hormonal contraceptive.
[3]Cycle phase estimated based on normalized cycle day; no samples were ovulatory based on absence of spinnbarketi by visual inspection.
[4]A Nugent core of 0-3 corresponds to "normal" (lactobasilli-dominated) microflora, 4-6 to "intermediate", and 7-10 to "bacterial vaginosis" (BV)—a condition associated with greater risk of STI acquisition. Assessment of Nugent scores was independently confirmed by the Clinical Microbiology and Immunology Lab at UNC.
[5]Values are expressed as mean ± SEM. Grey highlight indicates CVM samples containing sufficient native levels of anti-HSV-1 IgG to immobilize virions.

Figure 3:
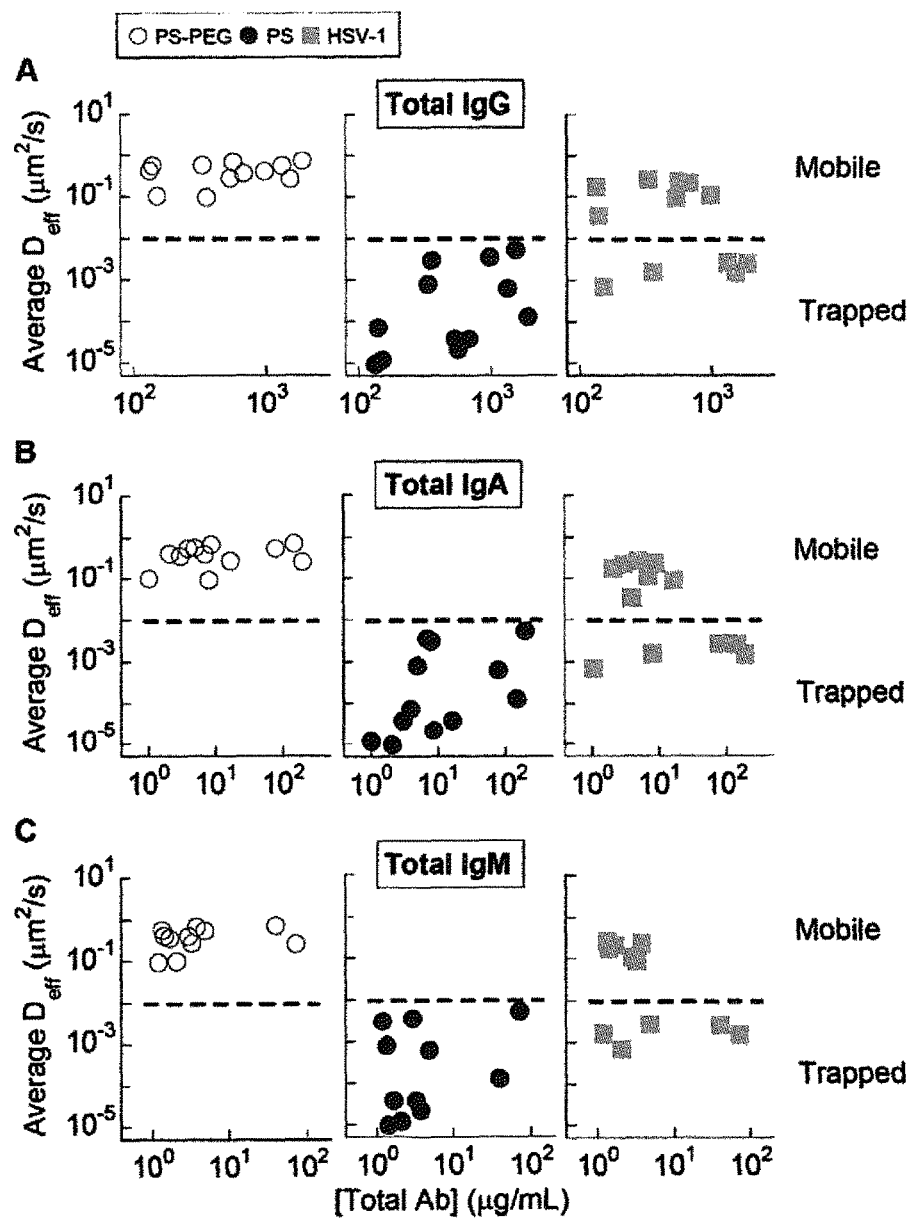
FIGS. 3A-3C show HSV-1 immobilization in CVM samples with elevated endogenous anti-HSV-1 IgG does not correlate with total IgG, IgA or IgM content. Geometric average $D_{eff}$($\tau=1$ s) for PS-PEG, PS and HSV-1 in individual CVM samples from unique donors (n=12) as a function of total endogenous (A) IgG, (B) IgA or (C) IgM. Dashed lines represent the $D_{eff}$ cutoff below which particles are permanently trapped (moving less than their diameter within 1 s).
Figure 4:
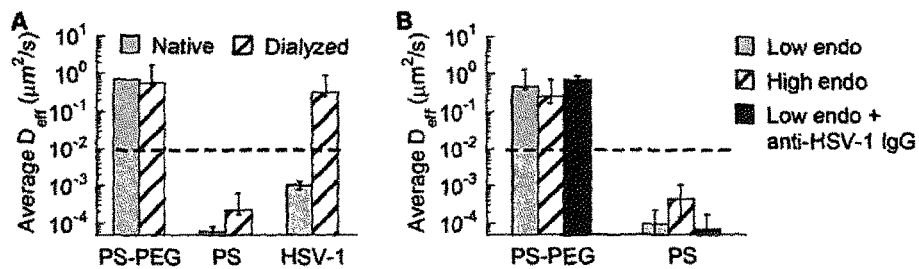
FIGS. 4A-4B show mobility of HSV-1, but not PS-PEG or PS, is influenced by anti-HSV-1 IgG levels in CVM. (A) HSV-1 is immobilized in native CVM samples with elevated endogenous anti-HSV-1 IgG, but becomes readily mobile in the same CVM specimens dialyzed to remove ~90-95% total IgG at constant sample volume. Control PS-PEG and PS particles remain diffusive and immobilized, respectively. Dashed line represents the $D_{eff}$ cutoff below which particles are permanently trapped (moving less than their diameter within 1 s). (B) The addition of exogenous anti-HSV-1 IgG to CVM samples with low levels of endogenous anti-HSV-1 IgG does not alter CVM's diffusional barrier properties to nanoparticles. Control PS-PEG and PS particles remained similarly diffusive and immobilized, respectively, in CVM with low endogenous ("Low endo"), high endogenous ("High endo") and exogenously added anti-HSV-1 IgG ("Low endo anti-HSV-1 IgG"). Differences in average $D_{eff}$ were not statistically significant for either PS-PEG or PS particles across the three conditions. Dashed line represents the $D_{eff}$ cutoff below which particles are permanently trapped (moving less than their diameter within 1 s).

Since IgG is the predominant immunoglobulin in human CVM (Usala et al., *J. Reprod. Med.* 34:292 (1989)), it was examined whether virion mobility correlated with endogenous virus-specific IgG in all 12 CVM samples using a whole-virus ELISA assay (Table 2). In good agreement with the hypothesis, HSV-1 diffused rapidly through all CVM samples that had little or no detectable endogenous anti-HSV-1 IgG (<0.2 µg/mL; detection limit 0.017 µg/mL) at rates only several-fold lower than their expected rates in water (FIGS. 1 and 2A). In contrast, in samples with elevated levels of endogenous anti-HSV-1 IgG (≥0.6 µg/mL), most HSV-1 virions were effectively trapped. HSV-1 that was trapped in place over the first 20 s observation remained trapped in the same locations for at least 15 min (FIG. 2B). In the same CVM samples, control latex nanoparticles comparable in size to HSV-1 and engineered with muco-inert coatings (PS-PEG; d~200 nm) exhibited rapid diffusion (FIGS. 1 and 2A), in good agreement with previous observations of the large pores present in human CVM (average~340 nm) ((Lai et al., *Proc. Natl. Acad. Sci. U.S.A.* 104:1482 (2007); Lai et al., *Proc. Natl. Acad. Sci. U.S.A.* 107:598 (2010)). Thus, the mucus mesh spacing was large enough for IgG-coated HSV-1 (at most 15-20 nm larger diameter even at saturation) to diffuse relatively unimpeded in the absence of adhesive interactions with mucin gel. Muco-adhesive latex nanoparticles of the same size (PS; d~200 nm) were markedly slowed or immobilized in the same CVM secretions (FIGS. 1 and 2A). Importantly, observations with PS-PEG and PS control particles confirmed that the general barrier properties of all samples, including those with low levels of endogenous anti-HSV-1 IgG, remained intact. HSV-1 mobility correlated only with endogenous HSV-1 specific IgG, and did not correlate with total IgG, IgA or IgM content (FIG. 3). After removal of ~90-95% of total IgG from these samples by dialysis at constant sample volume, HSV-1 became readily mobile (FIG. 4A), whereas PS beads remained immobilized (FIG. 4A).

TABLE 2

Characterization of CVM samples: Ab content.

| | Anti-HSV-1 IgG | | | | | | | | |
|---|---|---|---|---|---|---|---|---|---|
| Donor ID | Average | % of total | IgG$_1$ | IgG$_2$ | IgG$_3$ | IgG$_4$ | Total IgG | Total IgA | Total IgM |
| F10 | 0.92 ± 0.20 | 0.60% | 90% | 6.7% | 3.4% | N.D.[2] | 150 ± 12 | 1.0 ± 0.22 | 2.1 ± 1.7 |
| F12 | 0.66 ± 0.037 | 0.19% | 65% | 28% | 8.1% | 0.66% | 360 ± 36 | 8.1 ± 1.1 | 1.2 ± 0.91 |
| F14 | 1.9 ± 0.20 | 0.14% | 78% | 19% | 4.2% | 1.0% | 1300 ± 130 | 79 ± 9.3 | 4.8 ± 0.11 |
| F18 | 8.5 ± 0.31 | 0.56% | 71% | 20% | 6.1% | 4.5% | 1500 ± 110 | 200 ± 15 | 72 ± 6.9 |
| F9 | 23 ± 1.4 | 1.2% | 83% | 11% | 4.0% | 1.5% | 1900 ± 250 | 150 ± 21 | 39 ± 5.5 |
| Median | 1.9 | 0.56% | 78% | 19% | 4.2% | 1.0% | 1300 | 79 | 4.8 |
| SEM | 4.3 | 0.19% | 4.3% | 3.7% | 0.88% | 0.77% | 340 | 38 | 14 |
| F13 | 0.026 ± 0.00049 | 0.027% | 76% | 18% | 5.7% | 0.28% | 980 ± 79 | 7.0 ± 0.45 | 2.9 ± 1.3 |
| F15 | 0.080 ± 0.0011 | 0.024% | 68% | 29% | 4.1% | 0.28% | 330 ± 43 | 5.0 ± 0.91 | 1.4 ± 0.92 |
| F17 | 0.19 ± 0.023 | 0.036% | 49% | 34% | 20% | 0.67% | 540 ± 33 | 17 ± 1.5 | 3.3 ± 0.59 |
| F2 | 0.025 ± 0.0055 | 0.0044% | 67% | 27% | 9.2% | 0.0044% | 560 ± 40 | 8.9 ± 0.48 | 3.8 ± 0.44 |
| F21 | 0.018 ± 0.0063 | 0.013% | 70% | 27% | 4.0% | 0.056% | 140 ± 7.6 | 4.0 ± 0.16 | 0.085 ± 0.037 |
| F5 | 0.070 ± 0.011 | 0.010% | 91% | 6.4% | 1.9% | 0.41% | 680 ± 49 | 3.0 ± 0.31 | 1.7 ± 1.2 |
| F8 | 0.048 ± 0.030 | 0.036% | 67% | 28% | 5.0% | 0.021% | 130 ± 9.8 | 2.1 ± 0.20 | 1.4 ± 1.2 |
| Median | 0.048 | 0.013% | 68% | 27% | 5.0% | 0.28% | 540 | 5.0 | 1.7 |
| SEM | 0.023 | 0.0053% | 4.7% | 3.4% | 2.3% | 0.092% | 110 | 1.9 | 0.49 |

A well-recognized mechanism of mucosal immune defense is 'immune exclusion' in which microorganisms in the gut are agglutinated by secreted polyvalent IgA and IgM into clusters too large to diffuse through mucus (Hamburger et al., *Curr. Top. Microbiol. Immunol.* 308:173 (2006); Mantis et al., *Mucosal Immunol.* 4:603 (2011)). However, little to no agglutinated HSV-1 was in these experiments, consistent with previous findings that IgG is a relatively poor agglutinator (Berzofsky et al., In Fundamental Immunology. W. E. Paul, editor The Raven Press, New York, N.Y. 421 (1993)). Together, these observations suggest that individual HSV-1 virions in samples with elevated endogenous levels of anti-HSV-1 IgG are slowed or trapped by multiple low-affinity bonds with CVM rather than by physical (steric) obstruction.

Figure 5:
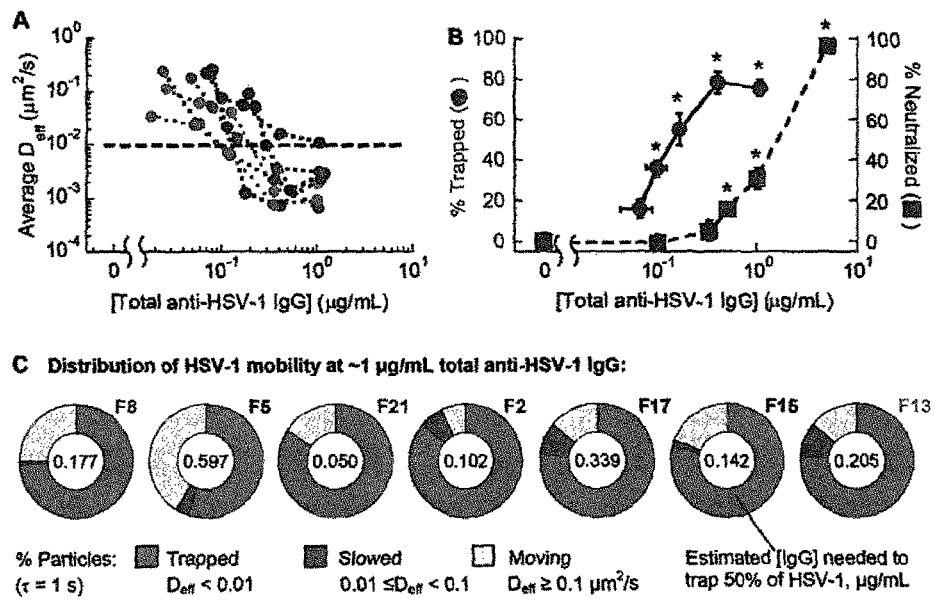
FIGS. 5A-5C show anti-HSV-1 polyclonal human IgG added to CVM samples with low endogenous anti-HSV-1 IgG potently traps HSV-1. HSV-1 mobility was quantified in aliquots of the same CVM samples with different amounts of anti-HSV-1 IgG added. (A) Comparison of effective diffusivity ($D_{eff}$; $\tau=1$ s) for HSV-1 in CVM samples (n=7, each experiment performed independently) with different amounts of total anti-HSV-1 IgG (sum of endogenous and added IgG). Different colored circles represent distinct samples. (B) In vitro neutralization vs. trapping potency of anti-HSV-1 IgG. Neutralization was assayed based on reduction of HSV plaque formation in Vero cells; trapping was defined as $D_{eff}$ ($\tau=1$ s) below 0.01 $\mu m^2/s$. Total IgG was averaged across samples for each treatment group. Error bars represent SEM. * indicates statistically significant difference compared to respective controls (p<0.05). (C) Distribution of particle speeds in samples treated with 1 μg/mL IgG (annulus chart), and estimated concentration of total IgG (μg/mL) needed for 50% trapping (number in center). Donor ID is indicated for each sample, with colors matching those in (A).
Figure 6:
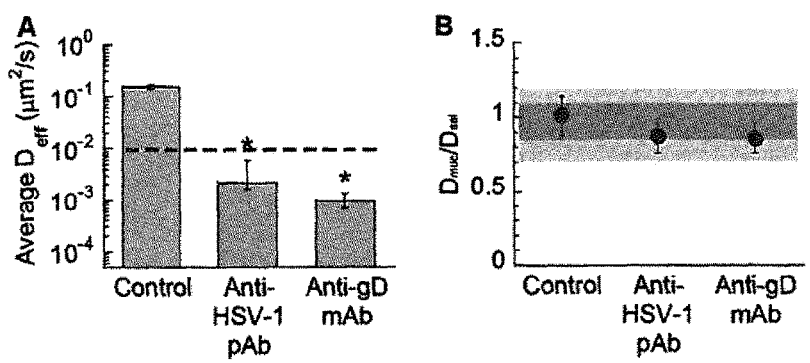
FIGS. 6A-6B show trapping HSV virions with polyclonal anti-HSV-1 and monoclonal anti-gD human IgG based on weak IgG-mucus interactions. (A) HSV-1 mobility in native CVM samples with low endogenous anti-HSV-1 IgG treated with 1 μg/mL polyclonal anti-HSV-1 IgG ("Anti-HSV-1 pAb"), monoclonal anti-gD IgG produced in 293 cells ("Anti-gD mAb") or anti-biotin monoclonal IgG produced in 293 cells ("Control"). Dashed line represents the $D_{eff}$ cutoff below which particles are permanently trapped (moving less than their diameter within 1 s). * indicates statistically significant difference compared to the Control group (p<0.01); the difference between the Anti-HSV-1 pAb and Anti-gD mAb groups was not statistically significant. (B) Ratio of diffusion coefficients in CVM vs. saline ($D_{muc}/D_{sal}$) for different Ab measured by fluorescence recovery after photobleaching (FRAP). For comparison, FITC-labeled human IgG ("Control") is included. Shaded regions indicate the range of values (dark grey=averages and light grey=average±standard deviation, respectively).

To confirm that trapping of HSV-1 in CVM was mediated specifically by IgG bound to virions and not by any other component in mucus that might be associated with elevated endogenous anti-HSV-1 IgG, HSV-1 specific IgG was affinity-purified from human intravenous immunoglobulin (starting with a pure clinical IgG preparation), and the purified IgG was mixed into CVM samples that had low endogenous anti-HSV-1 IgG. It was found that addition of 1 µg/mL anti-HSV-1 IgG trapped HSV-1 with a potency comparable to that of endogenous anti-HSV-1 IgG (FIG. 5; p<0.05 compared to native specimen without addition of anti-HSV-1 IgG). Lower anti-HSV-1 IgG doses were tested, and potent trapping of virions was observed when ~333 ng/mL anti-HSV-1 IgG was added (p<0.05), and partial trapping at 100 and 33 ng/mL anti-HSV-1 IgG added (both p<0.05). As controls, muco-adhesive PS remained markedly slowed or immobilized and muco-inert PS-PEG freely diffusive in CVM samples treated with the highest anti-HSV-1 IgG doses (FIG. 4B), confirming that the IgG did not cause HSV-1 trapping by altering mucus viscoelasticity or mesh spacing. Affinity-purified anti-HSV-1 IgG exhibited little neutralizing activity at 1 µg/mL and ~333 ng/mL (FIG. 5B), based on reduction of plaque formation in Vero cells, suggesting that multiple low-affinity bonds between IgG and CVM can trap virions at IgG levels lower than those needed to neutralize. HSV-1 was also trapped by a humanized monoclonal anti-gD IgG in CVM (FIG. 6A) but not by control, non-specific IgG (FIG. 6A), underscoring the specificity of trapping via particular antibody-virus pairs, rather than a non-specific interaction or alteration of general mucus barrier properties. In good agreement with previous studies (Olmsted et al., *Biophys. J.* 81:1930 (2001); Saltzman et al., *Biophys. J.* 66:508 (1994)), both polyclonal anti-HSV-1 IgG and monoclonal anti-gD IgG were only slightly slowed in CVM compared to saline (FIG. 6B), suggesting both antibodies form only transient, low-affinity bonds with CVM as individual molecules, yet facilitate effective trapping of virions once they accumulate on the viral surface by forming low-affinity but polyvalent IgG-mucin bonds.

Figure 7:
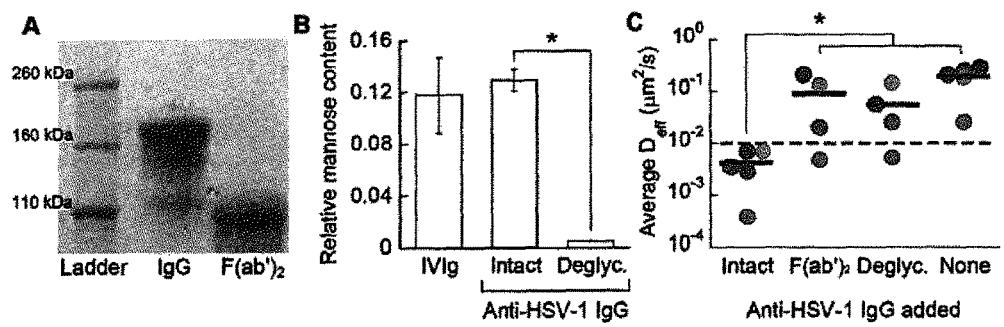
FIGS. 7A-7C show IgG-mucus interaction is Fc- and glycosylation-dependent. (A) Preparation of anti-HSV-1 F(ab')$_2$ confirmed by SDS-PAGE, (B) Preparation of deglycosylated anti-HSV-1 IgG confirmed by lectin-binding assay (absorbance of IgG-bound ConA normalized to amount of IgG). Error bars represent SEM. (C) Mobility ($D_{eff}$; τ=1 s) of HSV-1 in CVM with low endogenous anti-HSV-1 IgG incubated with various HSV-1 specific Ab: 1 μg/mL affinity-purified native IgG ("Intact"), 667 ng/mL F(ab')$_2$, and 1 deglycosylated IgG compared to HSV-1 in native CVM ("None"). Distinct samples (n=4-5, each experiment performed independently) are indicated with different color circles; averages are indicated by solid lines. Dashed line represents the $D_{eff}$ cutoff below which particles are permanently trapped (moving less than their diameter within 1 s). * indicates statistically significant difference (p<0.05).

It was next sought to determine the biochemical basis of the low-affinity bonds between IgG and CVM, The Fc domain of all IgGs harbors a conserved N-glycosylation site at Asn297, and many IgG effector functions are Fc- and Asn297 glycan-dependent (Ha et al., *Glycobiology* 21:1087 (2011)). Thus, F(ab')$_2$ fragments (FIG. 7A) and deglycosylated IgG (FIG. 7B) were prepared from the same affinity-purified anti-HSV-1 IgG to minimize any changes in HSV-1 binding avidity (confirmed by ELISA), and the mobility of HSV-1 pre-mixed with these modified analogs prior to addition to CVM (premixed to minimize interference by endogenous HSV-1 specific IgG) was measured. It was found that both F(ab')$_2$ and deglycosylated IgG exhibited substantially reduced trapping potency compared to intact IgG (FIG. 7C; p<0.05), suggesting that the low-affinity bonds IgG forms with mucins are not only Fc-dependent, but also influenced by Fc glycosylation.

Figure 8:
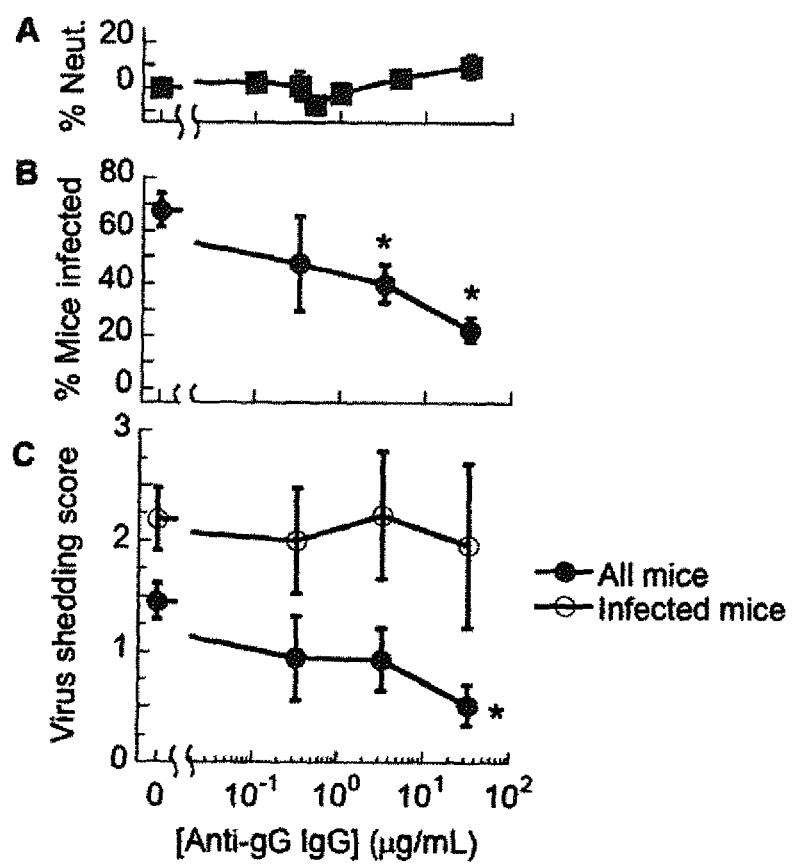
FIGS. 8A-8C show a non-neutralizing monoclonal IgG$_1$ against the gG epitope protects against vaginal HSV-2 infection in mice, without decreasing the extent of infection in mice that became infected. (A) In vitro neutralization of (% Neut.) vs. (B) in vivo protection against HSV-2. Neutralization was assayed based on reduction of HSV plaque formation in Vero cells. Depo-Provera®-treated mice were inoculated with HSV-2 mixed with control or anti-gG IgG. Infection was assayed three days post-inoculation by detection of virus in vaginal lavages using the ELVIS® HSV Test System. (C) Degree of HSV-2 shedding detected in vaginal lavages of all mice (filled circles), or of infected mice only (open circles). In vivo protection by 33 μg/mL anti-gG IgG is lost when mouse CVM is removed by gentle washing using a syringe pump. Data represent four independent experiments, each with n=10 mice per group. Error bars represent SEM. * indicates statistically significant difference compared to control (p<0.05).
Figure 9:
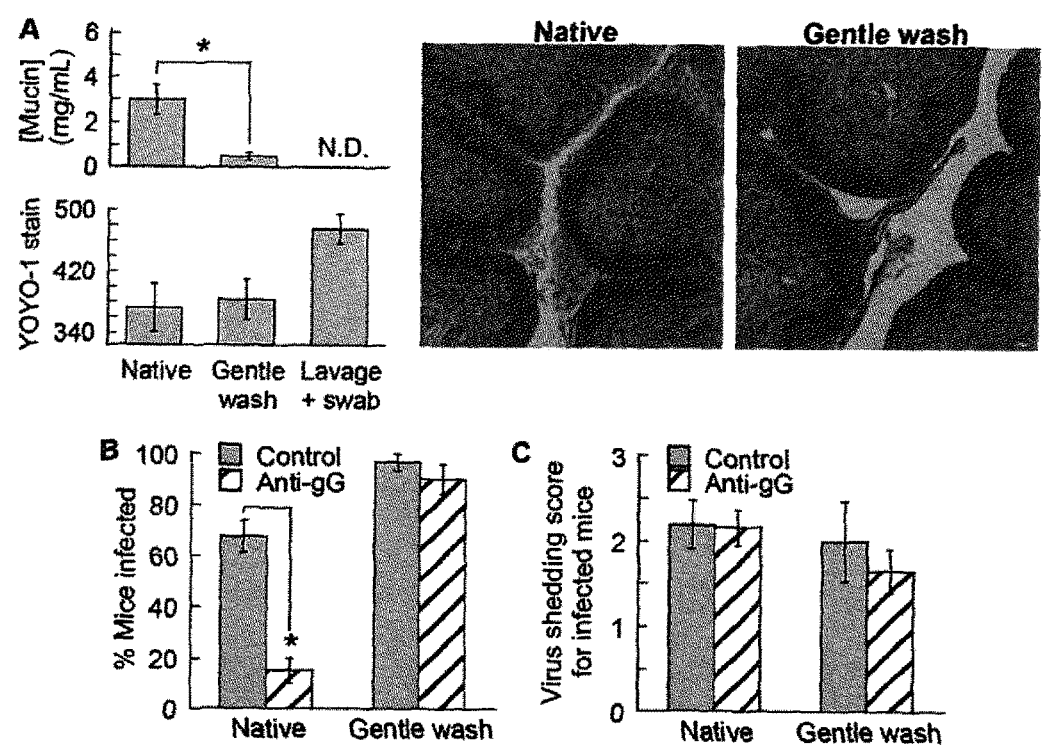
FIGS. 9A-9C show protection by anti-gG IgG$_1$ is lost when mouse CVM is removed by gentle vaginal wash. (A) Mucin concentration in vaginal fluid collected from the native or gently washed mouse vagina, YOYO-1 staining for vaginal epithelial cell damage in gently washed or conventionally lavaged and swabbed (cotton tip) mice, and H&E stained transverse sections of native vs. gently washed mouse vaginal tissue, N.D.=no data. (B) % infected among mice treated with 33 μg/mL anti-gG IgG with or without gentle washing to remove vaginal mucus. (C) The gentle wash did not alter the extent of infection in infected mice. Data represent at least three independent experiments, each with n=10 mice per group (total n=30-40 per group). Error bars represent SEM, * indicates statistically significant difference compared to control (p<0.05).

To determine whether trapping viruses in mucus can protect against infection in vivo, the ability of a non-neutralizing monoclonal IgG$_1$ to reduce HSV-2 transmission in the pH neutral mouse vagina was evaluated. This monoclonal IgG$_1$ binds to the relatively sparse gG surface glycoprotein, and exhibited no neutralization activity across all concentrations tested in vitro (FIG. 8A); mouse IgG$_1$ also possesses little to no complement (Ey et al., *Mol. Immunol.* 17:699 (1980); Michaelsen et al., *Scand. J. Immunol.* 59:34 (2004); Neuberger et al., *Eur. J. Immunol,* 11:1012 (1981)) and ADCC (Akiyama et al., *Cancer Res.* 44:5127 (1984); Kipps et al., *J Exp. Med.* 161:1 (1985)) activity. Mice were challenged vaginally with 2 ID$_{50}$ HSV-2 with and without anti-gG IgG$_1$, and HSV infection was assayed by detection of virus shedding in vaginal lavages three days post inoculation, a more sensitive assay of infection than visual observation of lesions, viral isolation from sacral ganglia, or death (Zeitlin et al., *Contraception* 56:329 (1997)). Anti-gG IgG$_1$, at a concentration of 3.3 µg/mL and above, significantly protected against infection and reduced the average viral load compared to either medium alone or control, non-specific IgG (FIGS. 8B and 8C, p<0.05). Interestingly, anti-gG IgG$_1$ appeared to only reduce the rate of successful vaginal HSV transmission; in mice that became infected, the extent of vaginal infection was comparable to that in mice receiving control IgG, suggesting that the anti-gG IgG dosed did not elicit effector functions that reduced the extent of virus spread in infected mice compared to control IgG (FIG. 8C), Protection was also evaluated in mice that received a gentle vaginal wash to remove mucus without detectable trauma to the epithelium (FIG. 9A). The removal of CVM increased susceptibility to HSV-2 in control mice from ~70% to ~100% (FIG. 9B) but not the degree of HSV shedding in mice that became infected (FIG. 9C). This moderate (~30%) increase in susceptibility is likely attributed to loss of innate protection by CVM itself: a CVM layer prevents immediate direct contact between viruses and the epithelium, and contains factors, such as defensins, that may further contribute to overall reduction infectious HSV flux to the epithelium. More importantly, removal of CVM completely abolished the ~50% extra protection (from ~70% to ~20% infection) afforded by anti-gG IgG$_1$ in native mice that cannot be attributed to innate immunity (FIG. 9B). Consistent with the hypothesis that trapping in mucus may facilitate protection, these results together suggest much of the observed synergistic enhancement in protection by anti-gG IgG$_1$ when CVM is present most likely occurred prior to HSV reaching target cells, rather than by immune mechanisms that can facilitate protection at the cellular level (e.g., complement or ADCC). These observations are also consistent with the poor complement and ADCC activity of mouse IgG$_1$, as well as numerous previous studies that have shown HSV can evade complement and other classical immune protective mechanisms (Brockman et al., *Vaccine* 26 *Suppl* 8:194 (2008); Hook et al., *J. Virol.* 80:4038 (2008); Lubinski et al., *J. Exp. Med.* 190:1637 (1999); Yuan et al., *Nature Immunol.* 7:835 (2006)). Since even a non-neutralizing monoclonal IgG against a relatively sparse surface antigen can afford substantial protection, monoclonals against more abundant surface antigens, such as gD and gB, or those optimized to maximize interactions with mucus are likely to provide even more potent protection at mucosal surfaces in vivo.

The first evidence of antibody-mucin affinity can be traced back more than 30 years, when Kremer and Jager noted that infertility in humans is often caused by anti-sperm antibodies (Jager et al., *Fertil. Steril.* 36:792 (1981); Kremer et al., *Fertil. Steril.* 27:335 (1976)). In cervical mucus samples with high levels of anti-sperm Ab, they found that both individual and agglutinated sperm make no forward progress and shake in place for hours until they die, despite vigorous flagellar motility. More recently, Phalipon et al. suggested secretory IgA can aggregate pathogenic *Shigella flexneri* in mouse nasal mucus secretions via the secretory component, anchoring the bacteria to the mucus gel and thereby 'excluding' them from infectious entry (Phalipon et al., *Immunity* 17:107 (2002)).

In both of the above instances, the authors assumed that the antibodies were attached firmly to the mucins. Similarly, the mucin-like Fcγ binding protein (FcγBP) has been proposed to serve an immunological role in mucus through its ability to bind strongly to IgG Fc (Kobayashi et at, *Gut* 51:169 (2002)). Nevertheless, more recent evidence indicates the primary function of FcγBP is instead to stabilize gastrointestinal mucus gel by covalently cross-linking Muc2 mucins (Johansson et at, *Proc. Natl. Acad. Set. U.S.A.* 108 *Suppl* 1:4659 (2011); Johansson et at, *J. Proteome Res.* 8:3549 (2009)). An IgG Fc-FcγBP-mucin crosslinking mechanism also directly contradicts numerous prior efforts that have failed to detect any significant binding of individual Ab to mucins (Clamp, *Biochem. Soc. Trans.* 5:1579 (1977); Cone, In Handbook of Mucosal Immunology. P. L. Ogra et al., editors. Academic Press, San Diego, Calif. 43-64 (1999); Crowther et al., *Fed. Proc.* 44:691 (1985); Olmsted et al., *Biophys. J.* 81:1930 (2001); Saltzman et al., *Biophys. J.* 66:508 (1994)). Indeed, previous FRAP experiments (Olmsted et al., *Biophys. J.* 81:1930 (2001)) and those here demonstrate that IgG and other Ab diffuse rapidly in human genital mucus, slowed only slightly compared to their diffusion in water. This can only be explained by weak and short-lived adhesive interactions between IgG and the mucin mesh, and not by the strong binding of IgG by FcγBP (Kobayashi et al., *J. Immunol.* 143:2567 (1989)). FcγBP also binds broadly to all IgG, and the interaction is thus subject to competitive inhibition (Kobayashi et at, *J. Immunol.* 143:2567 (1989)). In the present experiments where exogenous HSV-1 specific IgG was added to CVM, total levels of IgG already present in the samples were hundreds- to thousands-fold higher than the HSV-1 specific IgG doses added. Thus, for FcγBP to be responsible for the observed trapping phenomena, FcγBP must have been present in greater molar quantities than native IgG, which is unlikely given that the protein has not been routinely identified in proteomic screens of human genital tract fluid (see (Andersch-Bjorkman et al., *Mol. Cell. Proteomics* 6:708 (2007)) vs. (Dasari et al., *J. Proteome Res.* 6:1258 (2007); Shaw et al., *J. Proteome Res.* 6:2859 (2007); Tang et at, *J. Proteome Res.* 6:2874 (2007)). In contrast to previous studies, by examining the effect of IgG on virions in mucus gel rather than probing directly for interactions between individual IgG molecules and mucins, the present results document not only the potent trapping of individual virions by multiple surface-bound IgG, but also that the IgG-mucin interactions are Fc- and glycan-dependent.

Trapping virions in genital tract mucus should markedly reduce heterosexual transmission of viral infections. Women acquire many of the major sexually transmitted viral infections (e.g., HIV, HPV, and HSV) at rates on the order of 1 per 100 to 1,000 sex acts on average. This suggests few if any of these virions are able to infect target cells per intercourse, and therefore any reduction in the flux of virions that reach target cells should proportionally reduce transmission rates. Blocking initial infection altogether, rather than attempting to clear initial infections, may be especially critical for infections that are difficult, if not impossible, to cure once established (e.g., HSV, HIV). In the recent gD2-AS04 HSV vaccine trial (Belshe et al., *New Engl J. Med.* 366:34 (2012)), protective efficacy was initially observed in seronegative women but not in men or seropositive women, and a larger study of seronegative women revealed only moderate efficacy against HSV-1 (~35% efficacy against HSV-1 infection and 58% efficacy against HSV-1 genital disease) but interestingly no protection against HSV-2. In both studies, the vaccine elicited neutralizing serum Ab against HSV as well as HSV-specific cellular immune responses in all women and men. However, because mucosal levels of Ab were not monitored, it remains unclear whether what little protection was observed could have correlated with mucosal Ab response. It is likely that generating sufficient mucosal Ab levels remains a major bottleneck to an effective HSV vaccine. Inducing secreted Ab that bind to 'non-neutralizing' surface epitopes should trap pathogens as effectively as those that bind to neutralizing epitopes, a prospect that may broaden potential antigen targets for vaccine development, especially against virions with rapidly evolving neutralizing epitopes.

Example 2

Trapping of *Salmonella typhimurium* in Gastrointestinal Mucus

Figure 10:
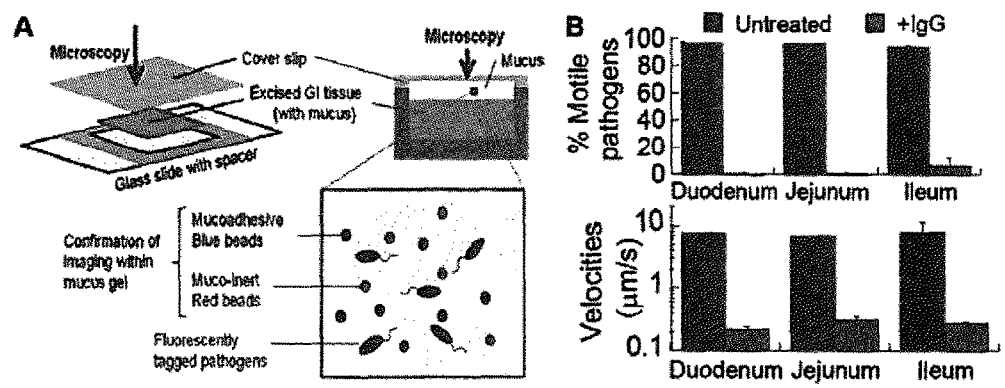
Figure 11:
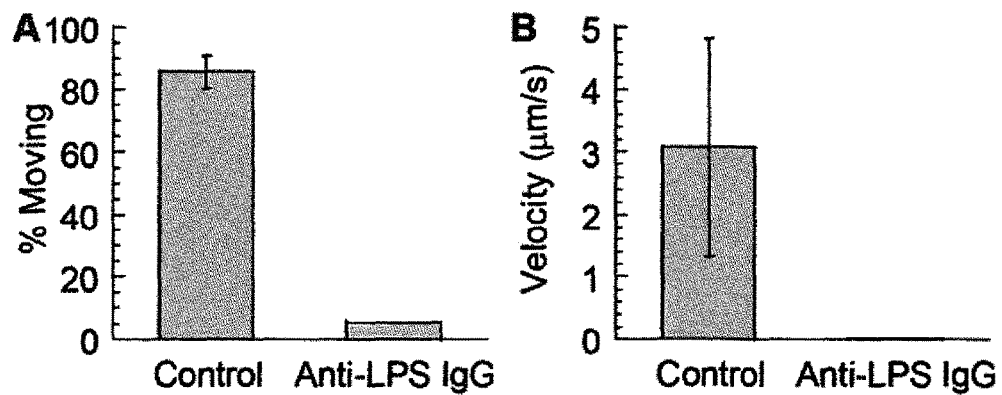
FIGS. 11A-11B show mobility of individual *Salmonella typhimurium* bacteria in control or anti-LPS monoclonal IgG-treated mouse gastrointestinal mucus. (A) Fraction moving and (B) average velocity. Note that average velocity for the anti-LPS IgG group is 0.036 μm/s, 85-fold lower than the average velocity for the control group.

Fe-mediated trapping of pathogens in mucus, which directly blocks infections at the portals of entry, may represent an exceptionally potent mechanism by which the immune system can rapidly adapt and reinforce multiple mucosal surfaces against diverse and rapidly evolving pathogens. A microscopy setup was developed that enables measuring bacterial mobility in real time directly in mucus overlaying intestinal epithelial tissue excised from mice (FIG. 10A). It was found that *Salmonella typhimurium* can readily penetrate undiluted mucus secretions coating the mouse gastrointestinal tract (duodenum, jejunum and ileum), but was effectively immobilized by topically applied anti-LPS and anti-flagella IgG (FIG. 10B). This immobilization occurred without inhibiting the flagella beating apparatus (Ab-coated *Salmonella* remained highly mobile in buffer) and without causing aggregation (i.e., independent of the classical, aggregation-based mechanism of immune exclusion (FIGS. 11A-11B). Furthermore, deglycosylated anti-LPS antibodies failed to trap the *Salmonella*, again highlighting the dependence of IgG-mucin interactions on Fc-N-glycans. These studies highlight the ability for IgG-mucin interactions to function at different mucosal surfaces, and act effectively on not just viral pathogens but also bacterial pathogens. The observed trapping in both CVM (predominantly Muc5b mucins) and gastrointestinal mucus (Muc2 mucins) suggests the molecular basis for Fe-mucin affinity is likely common among major secreted mucins— the long densely glycosylated fibers that form mucus gels— and possibly mediated by glycans, since sugars represent the major constituent of mucins (up to 80% by dry weight (Lai et al., *Adv. Drug Deliv. Rev.* 61:158 (2009))).

Example 3

Role of N-Glycans on IgG-Mucin Interactions

To further evaluate the role of N-glycans on IgG-mucin interactions, a number of anti-gD antibodies ("HSV8") with distinct glycosylation patterns were tested in the CVM assay of Example 1. Antibodies with distinct glycosylation profiles were produced in *Nicotiana benthamiana* plants using a viral-based transient expression system (magnICON). Transgenic *Nicotiana benthamiana*, in which plant-specific N-glycans (with core α1,3 fucose and β1,2 xylose) are reduced by RNAi inhibition of plant-specific glycosyltransferases and specific glycosyltransferases were over-expressed (e.g., β1,4 galactosyltransferase, see www.jbc.org/content/284/31/20479.full), were used as the host plant. Extract was clarified and IgG purified by protein A chromatography. Antibodies that were tested include HSV8-GnGn, in which contains about 95% of the antibodies contain the core structure with GlcNAc, mannose and terminal GlcNAc; HSV8-Gal, in which about 63% of the antibodies have either one or two terminal galactose sugar residues and about 5% have the GnGn core structure; HSV8-Agly, which is free of any glycosylation; and HSV8 produced in 293 cell cultures, which have the general diversity in glycosylation profiles found in humans. Note that HSV8-Gal represents the major serum IgG glycoform. We found that surprisingly, HSV8-Gal were substantially less potent at trapping viruses as HSV8-GnGn, which suggests antibodies that are engineered to have greater amount/extent of GnGn glycosylation vs. the naturally found Gal-terminated glycosylation is expected to be more potent at trapping virions. This observation not only further confirms the dependence on glycosylation, but underscores the importance of the precise nature of the glycosylation pattern.

The foregoing is illustrative of the present invention, and is not to be construed as limiting thereof. The invention is defined by the following claims, with equivalents of the claims to be included therein.

We claim:

1. An aerosol composition comprising a population of a human or humanized IgG monoclonal antibody directed against a virus that causes a respiratory disease, each antibody in the population comprising an oligosaccharide at a glycosylation site, the population comprising glycosylation patterns that enhance trapping potency of the antibody in mucus, wherein the antibody specifically binds an epitope of the virus, and wherein at least 30% of the antibodies in the population have a glycosylation pattern comprising the biantennary core glycan structure Manα1-6(Manα1-3)Manβ1-4GlcNAcβ1-4GlcNAcβ1 with terminal N-acetylglucosamine on each branch.

2. The aerosol composition of claim 1, wherein the glycosylation site is in an N-linked glycosylation site in an Fc region of the antibodies.

3. The aerosol composition of claim 1, wherein the epitope is a non-neutralizing epitope.

4. The aerosol composition of claim 1, wherein the epitope is a neutralizing epitope.

5. The aerosol composition of claim 4, wherein the antibody has trapping potency at a sub-neutralization dose.

6. The aerosol composition of claim 1, wherein the epitope is a conserved epitope.

7. The aerosol composition of claim 1, wherein the antibody comprises at least one Fc region.

8. The aerosol composition of claim 1, further comprising a second population of a second IgG monoclonal antibody, each antibody in the second population comprising an oligosaccharide at a glycosylation site, the second population comprising glycosylation patterns that enhance trapping potency of the second antibody in mucus, wherein the second antibody specifically binds a second epitope of the virus, wherein said second epitope is distinct from the epitope to which the first antibody specifically binds, or wherein the second antibody specifically binds an epitope of a target pathogen, wherein said target pathogen is different from the virus, wherein at least 30% of the antibodies in the second population have a glycosylation pattern comprising the biantennary core glycan structure Manα1-6(Manα1-3)Manβ1-4GlcNAcβ1-4GlcNAcβ1 with terminal N-acetylglucosamine on each branch.

9. A pharmaceutical composition comprising the aerosol composition of claim 1 and a pharmaceutically acceptable carrier.

10. A kit comprising the aerosol composition of claim 1.

11. The aerosol composition of claim 1, wherein the antibody reduces the mobility of at least 50% of the virus within mucus to at least one-tenth of its mobility in saline.

12. The aerosol composition of claim 1, wherein the antibody has a sufficient binding rate to an epitope of the virus to accumulate on the surface of the virus at sufficient levels to trap the virus in mucus within one hour at an antibody concentration of less than 100 µg/ml.

13. An aerosol composition comprising a population of a human or humanized IgG monoclonal antibody directed against a virus that causes a respiratory disease, each antibody in the population comprising an oligosaccharide at a glycosylation site, the population comprising glycosylation patterns that enhance trapping potency of the antibody in mucus, wherein the antibody specifically binds an epitope of the virus, and wherein the population comprises a sufficient amount of antibody having a glycosylation pattern comprising the biantennary core glycan structure Manα1-6(Manα1-3)Manβ1-4GlcNAcβ1-4GlcNAcβ1 with terminal N-acetylglucosamine on each branch for the concentration of the antibody having a glycosylation pattern comprising the biantennary core glycan structure Manα1-6(Manα1-3)Manβ1-4GlcNAcβ1-4GlcNAcβ1 with terminal N-acetylglucosamine on each branch in mucus after administration to a subject to be at least about 1 µg/ml.

14. An aerosol composition comprising a population of a human or humanized IgG monoclonal antibody directed against a virus that causes a respiratory disease, each antibody in the population comprising an oligosaccharide at a glycosylation site, the population comprising glycosylation patterns that enhance trapping potency of the antibody in mucus, wherein the antibody specifically bind an epitope of the virus, and wherein the population comprises a sufficient amount of antibody having a glycosylation pattern comprising the biantennary core glycan structure Manα1-6(Manα1-3)Manβ1-4GlcNAcβ1-4GlcNAcβ1 with terminal N-acetylglucosamine on each branch to trap the virus in mucus after administration to a subject.

* * * * *

UNITED STATES PATENT AND TRADEMARK OFFICE
CERTIFICATE OF CORRECTION

PATENT NO. : 10,100,102 B2
APPLICATION NO. : 14/438511
DATED : October 16, 2018
INVENTOR(S) : Lai et al.

Page 1 of 1

It is certified that error appears in the above-identified patent and that said Letters Patent is hereby corrected as shown below:

In the Specification

Column 28, Line 35: Please correct "35S" to read -- $^{35}S$ --

Column 30, Line 43: Please correct "IX" to read -- 1X --

Column 30, Line 47: Please correct "1x" to read -- 1X --

Column 33, Line 38: Please correct "(t)" to read -- ($\tau$) --

Column 33, Line 43: Please correct "a" to read -- $\alpha$ --

Column 33, Line 46: Please correct "a" to read -- $\alpha$ --

Column 37, Line 58: Please correct "Fe-" to read -- Fc- --

Column 38, Line 3: Please correct "Fe-dependent" to read -- Fc-dependent --

Column 38, Line 4: Please correct "Fe" to read -- Fc --

Column 39, Line 17: Please correct "Fey" to read -- Fc$\gamma$ --

Column 40, Line 31: Please correct "Fe-mediated" to read -- Fc-mediated --

Column 40, Line 55: Please correct "Fe-mucin" to read -- Fc-mucin --

In the Claims

Column 41, Claim 2, Line 49: Please correct "Fe" to read -- Fc --

Signed and Sealed this
Twenty-ninth Day of January, 2019

Andrei Iancu
*Director of the United States Patent and Trademark Office*